United States Patent
Montclare et al.

(10) Patent No.: US 9,453,060 B2
(45) Date of Patent: Sep. 27, 2016

(54) PROTEIN ENGINEERED SYSTEMS FOR DELIVERY OF MOLECULES

(71) Applicant: New York University, New York, NY (US)

(72) Inventors: Jin Kim Montclare, New York, NY (US); Haresh T. More, Ozone Park, NY (US); Joseph Frezzo, Brooklyn, NY (US); Carlo Yuvienco, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 14/910,794

(22) PCT Filed: Aug. 11, 2014

(86) PCT No.: PCT/US2014/050533
§ 371 (c)(1),
(2) Date: Feb. 8, 2016

(87) PCT Pub. No.: WO2015/021465
PCT Pub. Date: Feb. 12, 2015

(65) Prior Publication Data
US 2016/0185834 A1    Jun. 30, 2016

Related U.S. Application Data

(60) Provisional application No. 61/863,962, filed on Aug. 9, 2013.

(51) Int. Cl.
| | |
|---|---|
| C07K 14/47 | (2006.01) |
| A61K 47/42 | (2006.01) |
| A61K 48/00 | (2006.01) |
| A61K 9/127 | (2006.01) |
| A61K 9/00 | (2006.01) |
| C12N 15/113 | (2010.01) |
| A61K 47/10 | (2006.01) |

(52) U.S. Cl.
CPC ............. *C07K 14/47* (2013.01); *A61K 9/0014* (2013.01); *A61K 9/127* (2013.01); *A61K 47/10* (2013.01); *A61K 47/42* (2013.01); *A61K 48/0025* (2013.01); *C12N 15/1137* (2013.01); *C12N 2310/14* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 8,790,709 B2 * | 7/2014 | Montclare | A61K 9/1658 424/491 |
| 2011/0117141 A1 | 5/2011 | Huang et al. | |
| 2012/0251591 A1 | 10/2012 | Montclare et al. | |

FOREIGN PATENT DOCUMENTS

WO    2010/057155 A1    5/2010

OTHER PUBLICATIONS

Gunasekar, S.K., et al., N-Terminal Aliphatic Residues Dictate the Structure, Stability, Assembly, and Small Molecule Binding of the Coiled-Coil Region of Cartilage Oligomeric Matrix Protein, Biochemistry, Aug. 14, 2009, vol. 48, No. 36, pp. 8559-8567.
Wheeler, C.J., et al., A novel cationic lipid greatly enhances plasmid DNA delivery and expression in mouse lung, Proc. Natl. Acad. Sci. USA, Oct. 1996, vol. 93, No. 21, pp. 11454-11459.

* cited by examiner

*Primary Examiner* — Christina Bradley
(74) *Attorney, Agent, or Firm* — Hodgson Russ LLP

(57) ABSTRACT

Provided are compositions and methods for efficient delivery of polynucleotides and/or small molecules to or into cells. The compositions comprises a peptide which as an excess positive charge and self assembles into homopentamers. The homopentamers can non-covalently bind polynucleotides. When encapsulated in lipid systems, such as liposomes, the lipoproteoplexes so formed, are capable of delivering both nucleic acids and small molecules to cells.

17 Claims, 24 Drawing Sheets

Table 2

| | CSP·DNA (8:1) | | | | | |
|---|---|---|---|---|---|---|
| | Area (nm2) | Major (nm) | Minor (nm) | Angle | Circularity | Feret Diameter (nm) |
| 1 | 16.00 | 145.00 | 138.00 | 11.979 | 0.747 | 156.00 |
| 2 | 26.00 | 194.00 | 167.00 | 5.084 | 0.842 | 201.00 |
| 3 | 23.00 | 190.00 | 156.00 | 28.9 | 0.685 | 209.00 |
| 4 | 77.00 | 449.00 | 218.00 | 170.069 | 0.706 | 440.00 |
| 5 | 20.00 | 167.00 | 156.00 | 5.076 | 0.802 | 182.00 |
| 6 | 62.00 | 348.00 | 226.00 | 179.504 | 0.793 | 349.00 |
| 7 | 80.00 | 428.00 | 239.00 | 109.551 | 0.654 | 427.00 |
| 8 | 55.00 | 340.00 | 206.00 | 179.634 | 0.789 | 341.00 |
| 9 | 35.00 | 261.00 | 168.00 | 131.687 | 0.757 | 276.00 |
| 10 | 49.00 | 320.00 | 194.00 | 12.561 | 0.705 | 327.00 |
| 11 | 63.00 | 361.00 | 224.00 | 118.17 | 0.813 | 378.00 |
| 12 | 32.00 | 246.00 | 166.00 | 141.08 | 0.82 | 263.00 |
| 13 | 24.00 | 180.00 | 171.00 | 134.017 | 0.815 | 192.00 |
| 14 | 55.00 | 278.00 | 253.00 | 0.469 | 0.923 | 284.00 |
| 15 | 18.00 | 173.00 | 134.00 | 105.91 | 0.872 | 228.00 |
| 16 | 14.00 | 153.00 | 119.00 | 141.546 | 0.795 | 179.00 |
| 17 | 40.00 | 288.00 | 175.00 | 114.231 | 0.806 | 173.00 |
| 18 | 37.00 | 230.00 | 206.00 | 154.116 | 0.849 | 294.00 |
| 19 | 37.00 | 281.00 | 166.00 | 179.683 | 0.768 | 238.00 |
| Mean | 40.16 | 264.84 | 183.26 | 101.2246 | 0.786368 | 270.37 |
| SD | 20.41 | 91.48 | 37.43 | 67.25976 | 0.066692 | 84.72 |
| Min | 14.00 | 145.00 | 119.00 | 0.469 | 0.654 | 156.00 |
| Max | 80.00 | 449.00 | 253.00 | 179.683 | 0.923 | 440.00 |

Figure 11

| | FG·DNA (4:1) | | | | | |
|---|---|---|---|---|---|---|
| | Area (nm2) | Major (nm) | Minor (nm) | Angle | Circularity | Feret Diameter (nm) |
| 1 | 84.00 | 332.00 | 322.00 | 157.69 | 0.90 | 354.00 |
| 2 | 132.00 | 435.00 | 387.00 | 179.86 | 0.94 | 457.00 |
| 3 | 58.00 | 297.00 | 249.00 | 5.36 | 0.71 | 305.00 |
| 4 | 67.00 | 297.00 | 286.00 | 145.14 | 0.85 | 321.00 |
| 5 | 81.00 | 365.00 | 284.00 | 149.98 | 0.81 | 374.00 |
| 6 | 93.00 | 373.00 | 318.00 | 100.23 | 0.82 | 395.00 |
| 7 | 85.00 | 343.00 | 315.00 | 146.96 | 0.94 | 361.00 |
| 8 | 61.00 | 290.00 | 268.00 | 123.63 | 0.77 | 319.00 |
| 9 | 41.00 | 237.00 | 220.00 | 8.17 | 0.81 | 254.00 |
| 10 | 50.00 | 259.00 | 246.00 | 70.47 | 0.88 | 274.00 |
| 11 | 43.00 | 246.00 | 223.00 | 160.52 | 0.94 | 274.00 |
| 12 | 73.00 | 318.00 | 294.00 | 3.72 | 0.90 | 338.00 |
| 13 | 119.00 | 398.00 | 380.00 | 94.58 | 0.77 | 424.00 |
| 14 | 62.00 | 298.00 | 267.00 | 172.66 | 0.89 | 310.00 |
| 16 | 58.00 | 291.00 | 254.00 | 103.34 | 0.72 | 317.00 |
| 17 | 104.00 | 368.00 | 359.00 | 48.63 | 0.85 | 403.00 |
| 18 | 99.00 | 363.00 | 349.00 | 0.21 | 0.87 | 389.00 |
| 19 | 99.00 | 370.00 | 339.00 | 171.82 | 0.84 | 389.00 |
| 20 | 155.00 | 461.00 | 429.00 | 3.28 | 0.90 | 489.00 |
| 21 | 71.00 | 313.00 | 291.00 | 6.55 | 0.90 | 331.00 |
| 22 | 91.00 | 344.00 | 337.00 | 179.95 | 0.94 | 376.00 |
| 23 | 96.00 | 357.00 | 342.00 | 37.47 | 0.88 | 387.00 |
| 24 | 60.00 | 286.00 | 268.00 | 119.14 | 0.81 | 319.00 |
| Mean | 81.83 | 332.22 | 305.52 | 93.70 | 0.86 | 354.78 |
| SD | 28.45 | 56.58 | 54.42 | 66.18 | 0.07 | 58.43 |
| Min | 41.00 | 237.00 | 220.00 | 0.21 | 0.71 | 254.00 |
| Max | 155.00 | 461.00 | 429.00 | 179.95 | 0.96 | 489.00 |

Figure 11 (continued)

| CSP•DNA(8:1)•FG | | | | | |
|---|---|---|---|---|---|
| | Area (nm2) | Major (nm) | Minor (nm) | Angle | Circularity | Feret Diameter (nm) |
| 1 | 78.00 | 331 | 300 | 156.787 | 0.925 | 347 |
| 2 | 68.00 | 300 | 289 | 165.687 | 0.886 | 323 |
| 3 | 82.00 | 334 | 315 | 101.737 | 0.843 | 353 |
| 4 | 109.00 | 420 | 331 | 112.859 | 0.921 | 438 |
| 5 | 85.00 | 363 | 299 | 136.235 | 0.911 | 385 |
| 6 | 60.00 | 291 | 264 | 122.674 | 0.871 | 309 |
| 7 | 73.00 | 315 | 296 | 139.708 | 0.679 | 340 |
| 8 | 71.00 | 309 | 294 | 179.698 | 0.851 | 323 |
| 9 | 80.00 | 326 | 314 | 158.458 | 0.859 | 341 |
| 10 | 88.00 | 350 | 321 | 126.635 | 0.908 | 365 |
| 11 | 71.00 | 310 | 293 | 118.163 | 0.899 | 320 |
| 12 | 78.00 | 338 | 295 | 32.706 | 0.807 | 357 |
| 13 | 76.00 | 327 | 296 | 5.526 | 0.839 | 341 |
| 14 | 91.00 | 345 | 334 | 119.633 | 0.947 | 369 |
| 15 | 61.00 | 302 | 257 | 124.473 | 0.915 | 316 |
| 16 | 104.00 | 378 | 351 | 153.203 | 0.884 | 399 |
| 17 | 82.00 | 345 | 302 | 69.843 | 0.938 | 370 |
| 18 | 58.00 | 301 | 247 | 160.369 | 0.914 | 316 |
| 19 | 53.00 | 268 | 252 | 12.34 | 0.873 | 283 |
| 20 | 53.00 | 270 | 248 | 179.883 | 0.932 | 285 |
| 21 | 48.00 | 258 | 235 | 2.736 | 0.824 | 273 |
| 22 | 67.00 | 302 | 283 | 2.86 | 0.837 | 314 |
| 23 | 62.00 | 293 | 268 | 169.297 | 0.822 | 307 |
| 24 | 64.00 | 303 | 269 | 157.486 | 0.888 | 316 |
| 25 | 56.00 | 277 | 259 | 15.01 | 0.819 | 298 |
| 26 | 56.00 | 281 | 253 | 177.373 | 0.879 | 302 |
| 27 | 53.00 | 274 | 245 | 156.806 | 0.907 | 305 |
| 28 | 54.00 | 267 | 255 | 152.456 | 0.832 | 296 |
| 29 | 41.00 | 241 | 217 | 166.893 | 0.884 | 259 |
| 30 | 45.00 | 251 | 226 | 157.651 | 0.928 | 267 |
| 31 | 46.00 | 260 | 228 | 164.051 | 0.942 | 269 |
| 32 | 30.00 | 200 | 191 | 22.532 | 0.865 | 219 |
| 33 | 35.00 | 218 | 206 | 165.198 | 0.895 | 239 |
| 34 | 38.00 | 225 | 216 | 13.516 | 0.847 | 244 |
| Mean | 65.00 | 299 | 272 | 114.72 | 0.876 | 317 |
| SD | 19.00 | 47 | 39 | 61.856 | 0.053 | 47 |
| Min | 30.00 | 200 | 191 | 2.736 | 0.679 | 219 |
| Max | 109.00 | 420 | 351 | 179.883 | 0.947 | 438 |

Figure 11 (continued)

A. No Treatment Control

Phase contrast        Fluorescence

B. siRNA Only Control

Phase contrast        Fluorescence

C. (DOTAP:DOPE)•siRNA (10:1)

D. CSP•siRNA (5:1)

E. [(DOTAP:DOPE)+CSP]•siRNA (10:5:1)

F. (DOTAP:DOPE)•(CSP+siRNA) (10:5:1)

SEQUENCE LISTING

<160> NUMBER OF SEQ ID NOS: 10

<210> SEQ ID NO 1
<211> LENGTH: 61
<212> TYPE: PRT
<213> ORGANISM: artificial sequence
<220> FEATURE:
<223> OTHER INFORMATION: supercharged coiled-coil protein

<400> SEQUENCE: 1

Met Arg Gly Ser His His His His His His Gly Ser Gly Arg Leu Arg
1               5                   10                  15

Pro Gln Met Leu Arg Glu Leu Gln Arg Thr Asn Ala Ala Leu Arg Asp
            20                  25                  30

Val Arg Glu Leu Leu Arg Gln Gln Val Lys Glu Ile Thr Arg Leu Lys
        35                  40                  45

Asn Thr Val Arg Arg Ser Arg Ala Ser Gly Lys Leu Asn
    50                  55                  60

<210> SEQ ID NO 2
<211> LENGTH: 61
<212> TYPE: PRT
<213> ORGANISM: artificial sequence
<220> FEATURE:
<223> OTHER INFORMATION: supercharged coiled-coil protein

<400> SEQUENCE: 2

Met Arg Gly Ser His His His His His His Gly Ser Gly Asp Leu Ala
1               5                   10                  15

Pro Gln Met Leu Arg Glu Leu Gln Glu Thr Asn Ala Ala Leu Gln Asp
            20                  25                  30

```
Val Arg Glu Leu Leu Arg Gln Gln Val Lys Glu Ile Thr Phe Leu Lys
         35                  40                  45

Asn Thr Val Met Glu Ser Asp Ala Ser Gly Lys Leu Asn
     50                  55                  60
```

<210> SEQ ID NO 3
<211> LENGTH: 33
<212> TYPE: DNA
<213> ORGANISM: artificial sequence
<220> FEATURE:
<223> OTHER INFORMATION: primer

<400> SEQUENCE: 3
catcacggat ccggtcgtct gcgtccgcag atg                             33

<210> SEQ ID NO 4
<211> LENGTH: 18
<212> TYPE: DNA
<213> ORGANISM: artificial sequence
<220> FEATURE:
<223> OTHER INFORMATION: primer

<400> SEQUENCE: 4
gaactgcagc gtaccaac                                              18

<210> SEQ ID NO 5
<211> LENGTH: 17
<212> TYPE: DNA
<213> ORGANISM: artificial sequence
<220> FEATURE:
<223> OTHER INFORMATION: primer

<400> SEQUENCE: 5
gcgctgcgtg acgttcg                                               17

<210> SEQ ID NO 6
<211> LENGTH: 18
<212> TYPE: DNA
<213> ORGANISM: artificial sequence
<220> FEATURE:
<223> OTHER INFORMATION: primer

<400> SEQUENCE: 6
gaaatcaccc gtctgaaa                                              18

<210> SEQ ID NO 7
<211> LENGTH: 40
<212> TYPE: DNA
<213> ORGANISM: artificial sequence
<220> FEATURE:
<223> OTHER INFORMATION: primer

<400> SEQUENCE: 7
caccgttcgt cgttctcgtg cgtctggtaa gcttaattag                      40

<210> SEQ ID NO 8
<211> LENGTH: 19
<212> TYPE: DNA
<213> ORGANISM: artificial sequence
<220> FEATURE:
<223> OTHER INFORMATION: primer

<400> SEQUENCE: 8
tccacgacat actcagcac                                             19

```
<210> SEQ ID NO 9
<211> LENGTH: 18
<212> TYPE: DNA
<213> ORGANISM: artificial sequence
<220> FEATURE:
<223> OTHER INFORMATION: primer

<400> SEQUENCE: 9
aacgacccct tcattgac                                                   18

<210> SEQ ID NO 10
<211> LENGTH: 10
<212> TYPE: PRT
<213> ORGANISM: artificial sequence
<220> FEATURE:
<223> OTHER INFORMATION: modified HIV TAT

<400> SEQUENCE: 10

Arg Lys Lys Arg Arg Gln Arg Arg Arg Arg
1               5                   10
```

PROTEIN ENGINEERED SYSTEMS FOR DELIVERY OF MOLECULES

CROSS-REFERENCE TO RELATED APPLICATIONS

This application claims priority to U.S. Provisional application No. 61/863,962, filed on Aug. 9, 2013, the disclosure of which is incorporated herein by reference in its entirety.

BACKGROUND OF THE DISCLOSURE

A central challenge for gene therapy is the effective delivery of highly labile nucleic acids that are susceptible to nucleases. While there are examples of successful nucleic acid delivery in vitro and in vivo by viral and non-viral vectors, achieving high transfection efficiency while maintaining low toxicity remains a significant challenge. Although virus-mediated vehicles are efficient in gene transduction, they exhibit severe immunogenic properties and can cause detrimental mutagenic responses rendering them problematic.

Considerable effort has been made to develop non-viral vectors such as cationic lipids, cationic polymers, and cell-penetrating peptides (CPPs). Cationic lipids form non-covalent complexes with nucleic acids to generate lipoplexes. However, as the condensation ability of lipids alone is not effective, the resulting lipoplexes do not protect genes against nucleases in vivo. Cationic polymers such as poly-ethylenimine (PEI), poly (L-lysine) (PLL), polyamidoamine (PAMAM) dendrimers and polymethacrylates form particulate complexes with DNA producing polyplexes that can deliver genes. Although such polyplexes demonstrate r transfection ability, they exhibit high cytotoxicity. Moreover, chemical modifications to the cationic polymers are required to reduce their cytotoxicity. The resultant chemically modified polymers demonstrate decreased transfection ability. While CPPs have been explored for their ability to deliver nucleic acids, delivery remains a major challenge (Fonseca et al. Adv Drug Deliv Rev. 2009; 61:953-64) due to entrapment into endocytic vesicle and lysosomal degradation (Richard et al., J Biol Chem. 2003; 278:585-90; Al-Taei et al., Bioconjug Chem. 2006; 17:90-100. Recently, lipopolyplexes composed of a cationic lipid and cationic peptide-based ternary complex have been introduced to enhance transfection of nucleic acids (Zuhorn et al., Eur Biophys J. 2007; 36:349-62; Chen et al., Mol Pharm. 2009; 6:696-705). While lipopolyplexes have been employed for gene delivery, it depends on the development of branched systems carrying a net positive charge (Weiser et al., Mol Pharm. 2013; 10:127-41); in such cases, identifying optimal branching, charge and sequence will require various synthetic design strategies.

SUMMARY OF THE DISCLOSURE

This disclosure provides compositions and methods for delivery of polynucleotides, small molecules or both to cells. In this disclosure, provided are engineered supercharged coiled-coil proteins (CSP), derived from cartilage oligomeric matrix protein coiled-coil (COMPcc). Solvent exposed residues are mutated into arginine for effective binding to polynucleotides. The complexes so formed are highly positively charged and may be referred to herein as "lipoproteoplexes". These complexes may be used to deliver polynucleotides, small molecules, or both to cells. (FIG. 1).

In one aspect, this disclosure provides a peptide having a sequence of SEQ ID NO.: 1, and variants thereof.

In another aspect, this disclosure provides a composition comprising the peptide of SEQ ID NO.:1 or variants thereof. In one embodiment, the peptide or its variants are present as self-assembled homopentamers.

In one aspect, the disclosure provides complexes of polynucleotides and the homopentamers of peptide of SEQ ID NO.:1 (CSP) or its variants or variants of COMPcc (SEQ ID NO:2). In one embodiment, the polynucleotide is a polydeoxyribonucleotide (such as plasmid DNA). In one embodiment, the polynucleotide is a polyribonucleotide (such as an RNA molecule). In one embodiment, the polynucleotide may be a mixed molecule (heterogenous molecule containing both polyribonucleotide and polydeoxyribonucleotide backbones). In one embodiment, the polyribonucleotides or polydeoxyribonucleotides may be chemically modified. In one embodiment, the polynucleotides may comprise one or more polyribonucleotides, polyribonucleotides, mixed heterogenous polynucleotides, and/or chemically modified polynucleotides.

In one aspect, the disclosure provides a composition comprising complexes of polynucleotide and the peptide pentamers, which complexes are further complexed with transport materials. In one embodiment, the transport material comprises lipids, which may be cationic lipids, neutral lipids, or both. In one embodiment, the transport materials comprises cationic polymers. In one embodiment, the transport material comprises a combination of lipids and cationic polymers.

In one aspect, the disclosure provides a composition comprising lipoproteoplexes comprising pentamers of the peptide of SEQ ID NO.1 or variants thereof, polynucleotides, and a lipid composition. In one embodiment, the lipid composition comprises cationic lipids or neutral lipids. In one embodiment, the lipid composition comprises cationic lipids and neutral lipids. In one embodiment, the lipoproteoplexes further comprise small molecules (e.g., hydrophilic or hydrophobic small molecules). The small molecules may be complexed to the peptide/homopentamer or to the lipids or may be encapsulated, and/or incorporated into the lipid structures.

In one aspect, the disclosure provides a composition comprising complexes of homopentamers of the peptide of SEQ ID NO.1 or variants thereof, polynucleotides, and cationic polymers, and optionally lipid composition. The complexes may additionally also have small molecules.

In one embodiment, the complexes comprise homopentamers of the peptide of SEQ ID NO;1, cargo for delivery comprising polynucleotides (e.g., polyribonucleotides, polydexoyribonucleotides, or modifications thereof), small molecules (hydrophilic, hydrophobic or both) or both, and transport materials comprising lipids (cationic, neutral or both), cationic polymers or both.

In one aspect, the disclosure provides a method for delivery of cargo comprising polynucleotides, small molecules or both to cells. The method comprises preparing lipoproteoplexes of the polynucleotides and, optionally the small molecules, with homopentamers of a peptide of SEQ ID NO.:1 or variants thereof, contacting the target cells with the lipoproteoplexes under conditions such that delivery of the polynucleotides and small molecules in to the cells is effected.

In one aspect, the disclosure provides kits for delivery of cargo comprising polynucleotides, small molecules or both to cells comprising a composition comprising self assembled homopentamers of the peptide of SEQ ID NO.:1 or variants thereof, a transport material component comprising a lipid component and/or cationic polymer component, and instructions for preparation and use of the materials. In one embodiment, the kit also comprises small molecules which may be hydrophobic and/or hydrophilic. In one embodiment, the lipid component is made up of cationic lipids or neutral lipids. In another embodiment, the lipid composition is made up of cationic and neutral lipids. The various components may be supplied in different vials in the kit.

BRIEF DESCRIPTION OF THE DRAWINGS

FIG. 11. (Table 2) Particle size measurements of particles identified in FIG. 7 using ImageJ software.

DETAILED DESCRIPTION OF THE DISCLOSURE

Figure 1:
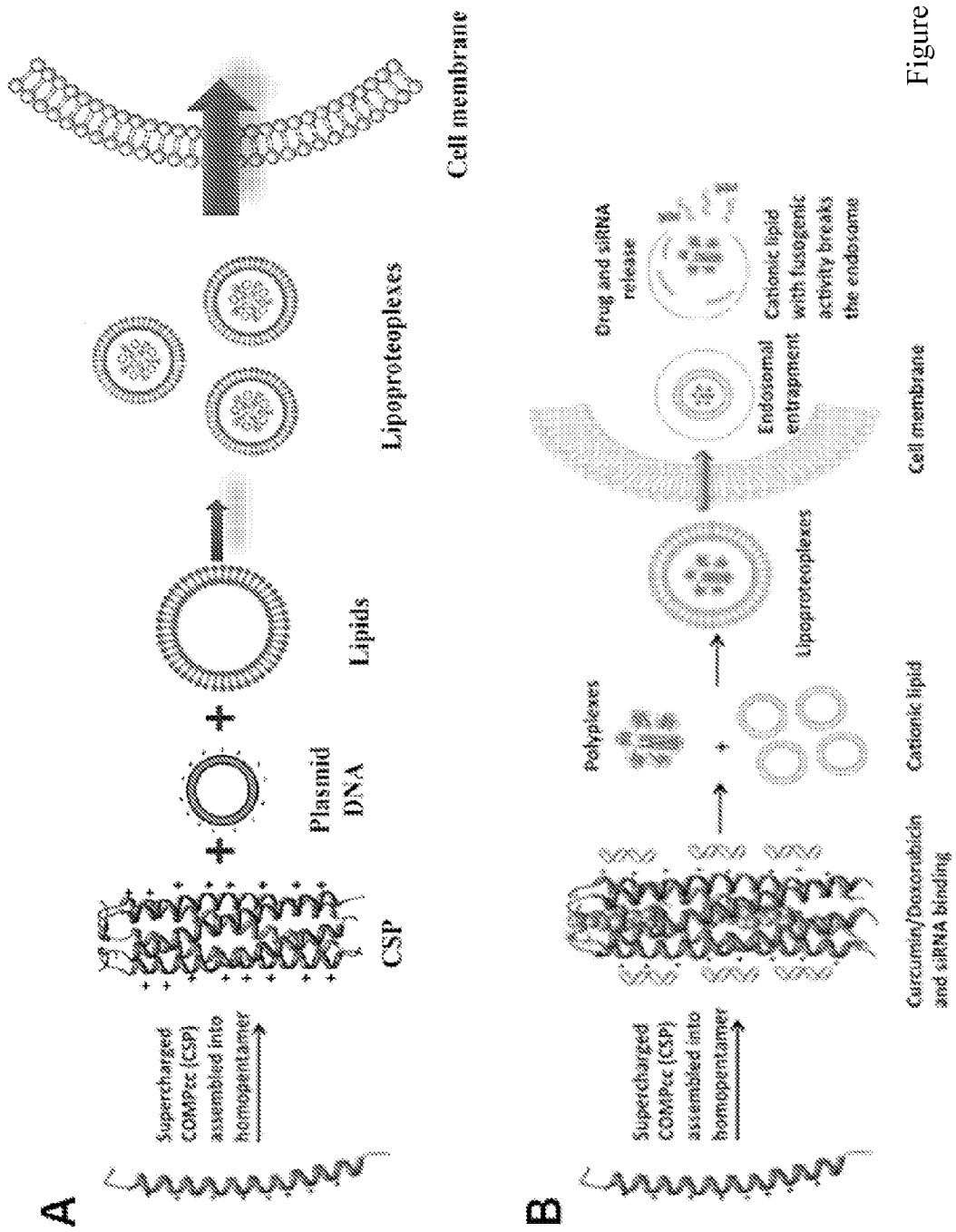
FIG. 1. Schematic of a process of the present invention showing CSP complexation with A) plasmid DNA or B) plasmid DNA+small molecule, and a ternary complex with cationic lipids to form lipoproteoplexes for gene delivery. C) Schematic of suggested mechanism by which liposomes encapsulate the proteoplexes. D) Schematic of an alternatively suggested mechanism by which proteoplexes non-covalently complex (via electrostatic forces) to the outer surface of cationic lipid assemblies.
Figure 1:
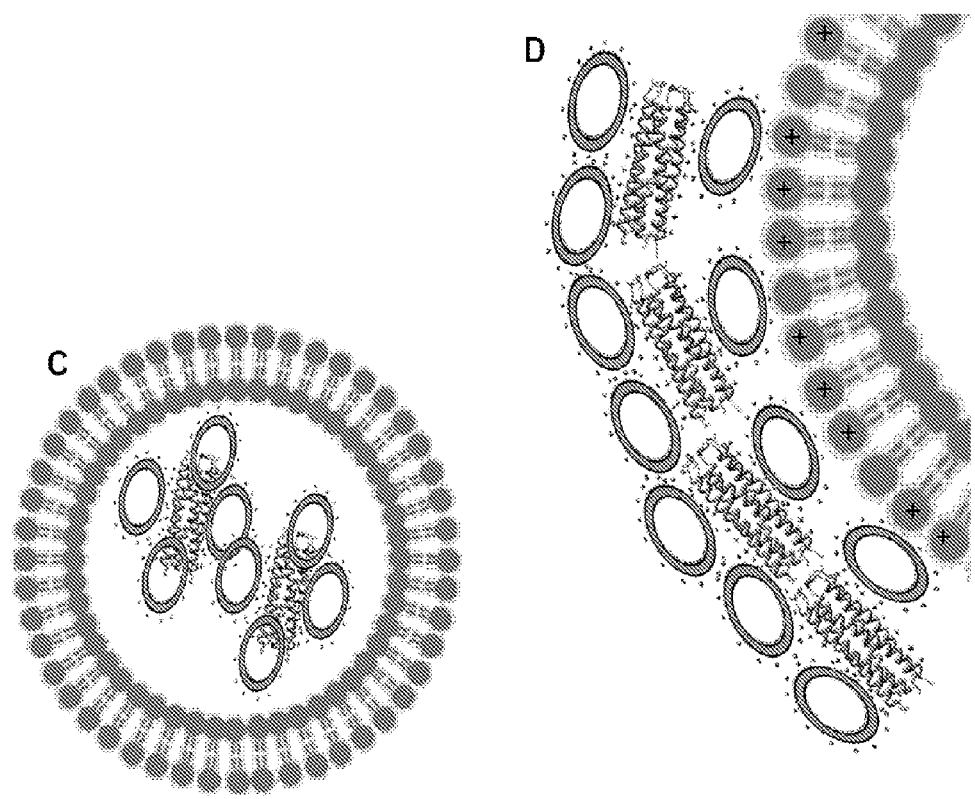

The present disclosure involves the fabrication of protein agents derived of cartilage oligomeric matrix protein coiled-coil (COMPcc) that self-assemble into homopentamers and that encapsulate drug molecules in the hydrophobic pore of the homopentamer through a non-covalent manner. In one embodiment, the surface residues of COMPcc, at b and c position of the heptad repeat of abcdefg, were mutated at eight different positions into arginine for effective binding to negatively charged DNA and for enhancement of cell penetration ability. The resultant supercharged COMPcc (CSP) indicated an alpha-helical structure.

The multifunctional protein/lipid system of the present disclosure is capable of: 1) encapsulating small molecules without the need of covalent modification; and 2) complexing with DNA effectively. Innovations in the protein engineered delivery system of the present disclosure include: a) the ease of integrating mutations enabling rapid optimization; b) dual drug and gene encapsulation; c) control over the delivery; and d) self-assembly.

An embodiment of the method of the disclosure is illustrated in FIG. 1(b) in which the supercharged COMPcc proteins are shown as assembled into a homopentamer that encapsulate the drug molecules (such as, for example, curcumin/doxorubicin) in a non-covalent manner and non-covalently complex with polynucleotides (such as, for example, siRNA) in conjunction with lipids as lipoproteoplexes, or in conjuction with cationic polymers. A number of the homopentamers form lipoproteoplexes which travel through the cell membrane of a targeted cell. Within the cell, the homopentamers release the small molecules and the siRNA, which then can act upon the targeted cell.

The peptides of the present disclosure are CSP8 or variants thereof or variants of COMPcc. The variants should be such that they form alpha helical structures and are able to self-assemble into homopentamers. For example, cationic buffers, pH 6-9, having buffering capacity in the 10 mM to 100 mM range, ionic strength on the scale of 100 mM NaCl will facilitate alpha helical structures.

The sequence of the CSP 8 (also referred to herein as CSP) and COMPcc suitable for use in the present invention is as follows:

CSP 8
M R G S H H H H H H G S G R L R P Q M L R E L Q
R T N A A L R D V R E L L R Q Q V K E I T R L K N
T V R R S R A S G K L N (SEQ ID NO:1)

COMPcc
M R G S H H H H H H G S G D L A P Q M L R E L Q
E T N A A L Q D V R E L L R Q Q V K E I T F L K N
T V M E S D A S G K L N (SEQ ID NO:2)

Bolded and underlined "R"s in SEQ ID NO:1 indicate where arginines were substituted for the amino acids in SEQ ID NO:2.

In one embodiment, variants of the COMPcc peptide are generated. For example, positional variation is permitted, but restricted, according to the design, to the b, c, and f residues as per the alpha-helical patterning of the protein's primary sequence. The variants are designed so as to maintain the hydrophobic pore of the pentamer and the helical structure.

The lipids useful for the present disclosure as transport materials are neutral lipids, cationic lipids, or combinations of cationic and neutral lipids. Thus, the lipid composition may be a cationic lipid, a neutral lipid, mixture of cationic lipids, mixture of neutral lipids, or a mixture of one or more cationic lipids with one or more neutral lipids.

Examples of cationic lipids include DOTMA (N-[1-(2,3-dioleoyloxy)-propyl]-N,N,N-trimethyl ammonium chloride), DOTAP (1,2-bis(oleoyloxy)-3-3-(trimethylammonium)propane), Dc-Cholesterol (3β-[N-(N'-dimethylaminoethane)-carbamoyl]cholesterol hydrochloride, DODMA (1,2-dioleyloxy-N,N-dimethyl-3-aminopropane), DMRIE (1,2-dimyristyloxypropyl-3-dimethyl-hydroxy ethyl ammonium bromide) or DDAB (dimethyl dioctadecyl ammonium bromide). Preferred polyvalent cationic lipids are lipospermines, specifically DOSPA (2,3-dioleyloxy-N-[2(sperminecarboxamido)ethyl]-N,N-dimethyl-1-propanaminium trifluoro-acetate) and DOSPER (1,3-dioleoyloxy-2-(6-carboxy spermyl)-propyl amide), and the di- and tetra-alkyl-tetra-methyl spermines, including but not limited to TMTPS (tetramethyltetrapalmitoyl spermine), TMTOS (tetramethyltetraoleyl spermine), TMTLS (tetramethlytetralauryl spermine), TMTMS (tetramethyltetramyristyl spermine), TMDOS (tetramethyldioleyl spermine), and combinations thereof.

Examples of neutral lipids include cholesterol, dipalmitoylphosphatidylcholine (DPPC), distearoylphosphatidylcholine (DSPC), phosphocholine (DOPC), dimyristoylphosphatidylcholine (DMPC), phosphatidylcholine (PLPC), phosphatidylethanolamine (PE), egg phosphatidylcholine (EPC), dilauryloylphosphatidylcholine (DLPC), dimyristoylphosphatidylcholine (DMPC), 1-myristoyl-2-palmitoyl phosphatidylcholine (MPPC), 1-palmitoyl-2-myristoyl phosphatidylcholine (PMPC), 1-palmitoyl-2-stearoyl phosphatidylcholine (PSPC), 1-stearoyl-2-palmitoyl phosphatidylcholine (SPPC), 1,2-distearoyl-sn-glycero-3-phosphocholine (DAPC), 1,2-diarachidoyl-sn-glycero-3-phosphocholine (DBPC), 1,2-dieicosenoyl-sn-glycero-3-phosphocholine (DEPC), palmitoyloeoyl phosphatidylcholine (POPC), lysophosphatidylcholine, dilinoleoylphosphatidylcholine distearoylphophatidylethanolamine (DSPE), 1,2-dioleoyl-sn-glycero-3phosphoethanolamine (DOPE), dimyristoyl phosphatidylethanolamine (DMPE), dipalmitoyl phosphatidylethanolamine (DPPE), palmitoyloeoyl phosphatidylethanolamine (POPE), lysophosphatidylethanolamine, a carbonyl methoxypolyethylene glycol-distearoyl phosphatidyl ethanolamine (MPEG-750-DSPE, -MPEG-2000-DSPE and MPEG-5000-DSPE), carbonyl methoxypolyethylene glycol-dipalmitoyl phosphatidyl ethanolamine (MPEG-2000-DPPE and MPEG-5000-DPPE), carbonyl methoxypolyethylene glycol-dimyristoyl phosphatidyl ethanolamine (MPEG-2000-DMPE and MPEG-5000-DMPE), and combinations thereof.

The lipid compositions can easily be prepared by routine methods or commercially available products can also be used. These include, for example, FuGene, Lipofectamine 2000, JetPEI, X-tremeGENE, and TransFast.

In one embodiment, the transport materials may be cationic polymers, including but not limited to polyethylenimine (PEI), polypropylenimine (PPI), poly-L-lysine, polyamidoamine (PAMAM), dendrimers and the like. In one embodiment, the transport materials may be cationic polymers and lipids (cationic and/or neutral lipids).

When the lipids comprise cationic and neutral lipids, the ratio of the two may vary as desired. In one embodiment, the ratio of cationic to neutral lipids is 10:1, 9:1, 8:1, 7:1, 6:1, 5:2, 4:2, 3:1, 2:1, 1:1 and all ratios from 10:1 and 1:1 to the tenth decimal place (such as, for example, 9.9:1, 9.8:1, 9:1.1, 9.1:1.1 and so on). In one embodiment, the ratio of cationic to neutral lipids is 1:10, 1:9, 1:8, 1:7, 1:6, 1:5, 1:4, 1:3, 1:2 and 1:1 and all ratios from 1:10 to 1:1 to the tenth decimal place.

The terms polynucleotides and nucleic acids are used interchangeably and refer to polyribonucleotides or polydeoxyribonucleotides, which may be modified or unmodified, single or double stranded. These molecules can be transfected using the present compositions and methods. For example, any type of DNA or RNA of any size and from any source may be used. The polynucleotides may comprise natural as well as non-natural bases. Shorter length polynucleotides (from 2-50 nucleotides) are often generally referred to as oligonucleotides. The polynucleotides or oligonucleotides may encode peptides or proteins, may exert inhibitory effect on other nucleic acids, may themselves have the ability to catalyze reactions, or may be useful for diagnostic purposes. Examples of molecules to be delivered include plasmid DNA, RNA interference molecules including siRNA, micro RNAs, anti-sense oligonucleotides, ribozymes, and the like.

In one embodiment, the cargo to be delivered comprises polynucleotides including polyribonucleotides, polydeoxyribonucleotides, mixed backbone (e.g., heterogenous polydeoxyribonucleotide and polyribonucleotide backbone), chemically modified polyribo- or polydeoxyribonucleotides, and combinations thereof. The molecules may be single stranded or double stranded, or may be circular or partially circular.

In one embodiment, the ratio of lipid (or cationic polymer) to polynucleotide (w/w) is from 5:1 to 20:1 and all ratios therebetween to the tenth decimal place and all ranges of ratios therebetween. In various embodiments, the ratio of lipid to polynucleotide (w/w) is 6:1, 8:1, 10:1, 12:1, 14:1, 16:1, 18:1.

In addition to the nucleic acids, the present compositions can also, additionally or alternatively, deliver small molecules, such as, for example, hydrophobic and/or hydrophilic drugs. Examples of drugs include, but are not limited to, Curcumin, doxorubicin, all-trans retinol, vitamin D, retinoid antagonists/inverse agonists, taxol, steroids, peptides, other anticancer and antiarthritis drugs, and the like.

The present peptides, which can self-assemble, have the ability to deliver small molecules, and nucleic acids (such as siRNA) to or into a cell so as to have a synergistic effect on the disease condition and this leads to a bio-based delivery vehicle. A variety of chemical agents and genes alone or in combination can be delivered to, for example to, gain insight into cell organism functions. Moreover, a targeted delivery of a therapeutic cargo can be established by conjugating to the cell targeting antibodies and peptides. In addition, as the proteins are fabricated in the cell, the synthetic conditions are free of organic solvents that are commonly used for synthetic constructs. This provides a unique advantage for applications in the biomedical arena as there is no need to remove/purify from toxic organic media, and concerns of organic contamination or biodegradability are negligible.

A complex of the peptide (homopentamer) and the polynucleotide or the lipid component and the polynucleotide or any other combination of components may be indicated herein by the symbol "•". CSP•DNA(8:1) (indicating a complex of CSP and DNA) showed aggregate structures with an average Feret diameter of 270.4±84.7 nm, where Feret diameter is the distance between two parallel planes restricting the dimensional boundaries of the measured object. A drastic change in shape, size and overall morphology of the complex was observed in presence of FuGene (FG); the FG•DNA(4:1) and CSP•DNA (8:1)•FG showed small spherical particles with a ferret diameter of 354.8±58.4 nm and 317±47 nm, respectively. In general, the CSP•polynucleotide•lipid complex will range in size, depending on the lipid formulation, within 100-500 nm as measured by both spectroscopic and microscopic visualization techniques. In embodiments, the Feret diameter of the complexes is from 100 to 500 nm and all integers therebetween. In specific embodiments, the Feret diameter of the complexes is 150, 200, 250, 300, 350, 400, 450 and 500 nm. In specific embodiments, the Feret diameter is from 200-400 nm. Particle size measurements are known in the art. For example particle size may be measured by transmission electron microscopy (to measure Feret diameter) or by dynamic light scattering.

In the present invention the polynucleotide, such as, for example, DNA is complexed to the peptide homopolymer by non-covalent interactions. Additionally, the present protein also binds non-covalently to small molecules. While not intending to be bound by any particular theory, it is considered that the present protein may non-covalently bind or encapsulate small molecules into the hydrophobic pore of the protein.

The supercharged protein of the present invention self-assembles and binds to DNA and small molecules individually, or in combination. Thus, the protein of the present invention shows binding to genes and small molecules and can be used for therapeutic protein delivery.

In certain embodiments, the present invention is a dual gene and drug delivery vehicle. The supercharged protein of the present invention is developed from a natural protein with certain mutations and is biodegradable as compared to synthetic polyethylenimines Additionally, the supercharged protein of the present invention maybe developed from bacterial expression, is biodegradable, and has ability to bind to small molecules and nucleic acids at the same time.

In one aspect, the present disclosure provides compositions suitable for delivering materials to cells. The compositions comprise one or more peptides disclosed herein in suitable carriers. Suitable carriers for use in such compositions are known in the art. Examples of suitable carriers for administration include water, saline solution, buffer solutions such as phosphate buffers, glycine solutions and the like. Suitable carriers for in vitro use include all of the above and standard culturing media including DMEM, α-DMEM, with or without serum such as fetal bovine serum.

Suitable carriers include, for example, a diluent, adjuvant, excipient, or other vehicle with which the present complexes may be administered to an individual. The formulations may be in an injectable form (for administration via any of the standard injectable routes) to an individual. The individual may be a human being or a non-human animal Some examples of materials which can serve as pharmaceutically-acceptable carriers include: sugars, such as lactose, glucose and sucrose; starches, such as corn starch and potato starch; cellulose, including sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. The composition, if desired, can also contain minor amounts of wetting or emulsifying agents, or pH buffering agents. Some examples of compositions suitable for mixing with the agent can be found in: Remington: The Science and Practice of Pharmacy (2005) 21st Edition, Philadelphia, Pa. Lippincott Williams & Wilkins. In one embodiment, the agent is substantially purified (e.g., substantially free from substances that limit its effect or produce undesired side-effects).

In embodiments, the compositions may be formulated for topical, transdermal, or mucosal use. Such formulations include, for example, powders, sprays, ointments, pastes, creams, lotions, gels, solutions, patches, and inhalants. The components of the present disclosure may be mixed under sterile conditions with a pharmaceutically-acceptable carrier, and with any preservatives, buffers, or propellants which may be required. The ointments, pastes, creams and gels may contain additional excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Topical powders and sprays may also contain additional excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

In one embodiment, a 3D collagen based matrix may be used. In one embodiment, transdermal patches may be used. These have the added advantage of providing controlled delivery to the body. Such dosage forms can be made by dissolving or dispersing the agent in the proper medium. Absorption enhancers can also be used to increase the flux of the active ingredient across the skin. The rate of such flux can be controlled by either providing a rate controlling membrane or dispersing the active ingredient in a polymer matrix or gel. In one embodiment, the compositions are applied to dermal patches, bandages, gauges or other similar materials that can be directly applied to a desired area.

The following examples further describe the disclosure. These examples are intended to be illustrative and not limiting in any way.

EXAMPLE 1

This examples describes preparation, and characterization of a peptide of the present invention. In this example, a CSP is expressed, purified and assessed for its secondary structure and binding ability to DNA. Data is provided for in vitro delivery of an exemplary polynucleotide β-galactosidase gene) into MC3T3-E1 mouse preosteoblasts. The CSP and lipoproteoplex are evaluated for cytotoxicity against MC3T3-E1 cells. Also, CSP•DNA complex and lipoproteoplexes are further characterized for their size, surface charge and morphology.

Materials and method. Materials. Primers were purchased from Eurofin MWG Operon (Huntsville, Ala.), pfu Ultra DNA polymerase from Stratagene (Santa Clara, Calif.) and DpnI restriction enzyme from New England Biolabs (Ipswich, Mass.). Tris base, isopropyl β-D1-thiogalactopyranoside (IPTG), tryptone, ampicillin, sodium chloride, imidazole and urea were obtained from VWR. Ni-NTA beads were purchased from Sigma-Aldrich, β-galactosidase plasmid DNA from Genlantics (San Diego, Calif.) and Beta-Glo assay kit from Promega, (Madison, Wis.). Gibco alpha minimal essential medium (αMEM), Gibco fetal bovine serum (FBS), 5000 U/mL penicillin and 5000 ug/mL streptomycin were purchased from Invitrogen (Carlsbad, Calif.). FG was obtained from Roche (Branchburg, N.J.) and the HIV-1-Tat (RKKRRQRRRR) (SEQ ID NO:10) modified (mTat) with ten histidine residues and two cysteine residues (C-5H-Tat-5H-C) was purchased from Biomatik Corporation (Cambridge, Canada).

Site-directed mutagenesis (SDM) and PCR assembly. The COMPcc gene in pQE9 vector was used as a template to perform multiple mutations. The residues at D28, A30, E39, Q45, F60, M66, E67 and D69 were mutated to arginine by using following primers and their complementary sequences. D28R and A30R/5'-CAT CAC GGA TCC GGT CGT CTG CGT CCG CAG ATG-3' (SEQ ID NO:3); E39R/ 5'-GAA CTG CAG CGT ACC AAC-3' (SEQ ID NO:4); Q45R/5'-GCG CTG CGT CGT GAC GTT CG-3' (SEQ ID NO:5); F60R/5'-GAA ATC ACC CGT CTG AAA-3' (SEQ ID NO:6); M66R, E67R and D69R/5'-C ACC GTT CGT CGT TCT CGT GCG TCT GGT AAG CTT AAT TAG-3' (SEQ ID NO:7). The DNA fragments with required mutations were synthesized by PCR by using forward primer of one mutant and reverse primer of the following mutant. The resulting gene bearing all 24 base pairs mutations was used as a megaprimer for mutagenesis of pQE9/COMPcc to produce pQE9/CSP. Site directed mutagenesis SDM was performed using a standard protocol and the resulting sample was digested with DpnI enzyme (New England Biolabs) for 3 hours at 37° C. The DpnI digested sample was transformed into XL-1 blue cells.

Protein expression and purification. To express the CSP and COMPcc proteins, the *E. coli* strains AF-IQ and XL-1 blue were used for transformation of CSP and COMPcc, respectively. Starter culture of CSP and COMPcc were made in 5 mL of LB containing ampicillin (200 μg/mL) and chloramphenicol (35 μg/mL) and LB containing ampicillin (200 μg/mL), respectively and incubated overnight at 37° C. and 350 rpm. The starter cultures were used to innoculate 800 mL of LB media with the aforementioned respective antibiotics and incubated for 6 hours at 37° C. and 250 rpm for large scale expression. After 6 hours, $OD_{600}$ was measured (≈0.8 to 1.0) and the protein expression was induced by the addition of 200 μg/mL IPTG and incubated under the same conditions for 3 hours. Cells were harvested after overexpression by centrifugation and stored at −80° C. until purification. Overexpression was confirmed by SDS-PAGE (FIG. S1a). The cells pellets were thawed and resuspended into 50 mM Tris-HCl buffer pH 8.0 with 0.5 M NaCl, 20 mM imidazole and 6 M urea and lysed via sonication. Whole cell lysates were clarified by centrifugation and purified under native condition using Ni-NTA beads. Purification was performed in a 10 mL gravity column (Thermo Scientific). The beads were washed with the buffer composed of 50 mM Tris-HCl, 0.5 M NaCl and 20 mM imidazole and the protein was eluted with increase concentration of imidazole from 200 mM, 500 mM and 1 M imidazole. The purity of the proteins was confirmed by SDS-PAGE (FIG. S1b and FIG. S1c). The proteins were dialyzed against 50 mM Tris-HCl buffer pH 8.0 with 0.5 M NaCl to remove the imidazole.

CD spectroscopy. The secondary structure of CSP/COMPcc was analyzed using a Jasco J-815 spectrometer at 10 μM protein concentration in 50 mM Tris-HCl buffer pH 8.0. The wavelength scans were performed at 4° C. over a range of 200-250 nm with a 1 nm step size. Temperature scans were performed at 222 nm from 20° C. to 85° C. with temperature ramp of 1° C./min The observed ellipticity value ($\Theta$) was converted into mean residue ellipticity (MRE) using the standard equation $\Theta_{MRE}=\Theta/(10\ cpl)$ where c is the molar concentration of the protein, p is the path length in centimeters and l is the number of amino acids. The fraction folded was derived using equation $F=(\Theta_A-\Theta_U)/(\Theta_N-\Theta_U)$, where, $\Theta_A$ is the MRE observed at given temperature, $\Theta_U$ is MRE value for completely unfolded protein and $\Theta_N$ is the MRE value of completely folded protein that is considered at 25° C. The first derivative of fraction folded was used to calculate melting temperature ($T_m$) of protein. All data were represented as an average of three trials.

Electrophoretic mobility shift assay and lipoproteoplex preparation. Plasmid DNA encoding β-galactosidase (gWiz β-galactosidase) under the control of the cytomegalovirus promoter/enhancer was used to investigate protein binding and also acted as a reporter for successful transfection. The β-galactosidase plasmid DNA (5.1 kb) at a concentration of 50 ng was mixed with different concentrations of CSP and COMPcc and incubated at room temperature for 30 minutes. The mixtures were run on 1% agarose gel (stained with ethidium bromide) and imaged under UV light using ImageQuant (GE healthcare). The lipoproteoplex was prepared by mixing the FG at 4:1 w/w ratio of lipid•DNA with an already formed condensed mixture of plasmid DNA and CSP/COMPcc and the ternary complex was incubated for 15 minutes at room temperature.

Transfection studies. The transfection studies were performed using β-galactosidase plasmid DNA. The MC3T3-E1 were seeded in 96-well plate at a density of $1\times10^4$ cells/well in αMEM with 10% FBS, 5000 U/mL penicillin and 5000 ug/mL streptomycin for 24 hours prior to experiment. The proteoplex and lipoproteoplexes were prepared as explained above at different CSP•DNA w/w ratios of 5:1 and 8:1. The mixtures were added to different wells and incubated for 24 hours at 37° C. at 5% (v/v) $CO_2$. As a negative and positive control, plasmid DNA alone and FG•DNA(4:1) were also prepared, respectively. Based on previous studies using mTat•DNA(10:1)•FG lipopolyplexes, the optimized component mixture was also used as a positive control. The expression of β-galactosidase was confirmed using a standard Beta-Glo assay kit provided by manufacturer. The luminescent signal obtained after reaction of β-galactosidase with Beta-Glo reagent was observed using the microplate reader Synergy™ HT (BioTek Instruments, Winooski, Vt.). Data were expressed as mean β-galactosidase activity (relative light units, RLU) per well±standard deviation from quadruplicates. This detection system is designed to measure directly the expression level using 96-well plates.

Cell viability studies. The cells were seeded in 96-well plate at a density of $1\times10^6$ cells/well in αMEM with 10% FBS and incubated at 37° C. with 5% $CO_2$ overnight. The cytotoxicity of different complexes was evaluated by 3-(4, 5-dimethylthiazol-2-yl)-2,5-diphenyl tetrasodium bromide, MTT assay. Approximately 10 μL of MTT reagent from 5 mg/mL stock was added to each well and incubated for 4 hours at 37° C. with 5% $CO_2$. After incubation, the entire medium was aspirated and 100 μL of dimethyl sulfoxide was added to each well. The change in absorbance of colored solution was observed using a microplate reader Synergy HT at 570 nm. The percent cell viability was calculated by normalizing the observed absorbance value to that of the control cells without any treatment. The data was represented as the average of quadruplicates±standard deviation.

Zeta potential. Zeta potential of protein, plasmid DNA and complex was determined using Zetasizer Nano ZS90 (Malvern Instruments, UK) with a laser source of 630 nm. The instrument calculates the zeta potential based on the measured electrophoretic mobility and this is fit into a Smoluchowski equation. The plasmid DNA alone was prepared at 90 ng/μL and for other mixtures the DNA was kept at a final concentration of 2.5 ng/μL with 8 times higher concentrations of CSP/COMPcc and 4 times the concentration of FG. For protein and FG alone, the concentrations were at 59.7 ng/μL and 18.7 ng/μL, respectively. All samples were prepared in 0.22 nm filtered $dH_2O$ and the ionic strength was kept constant for all solutions with approximate concentration of buffer as 2.7 mM with 27.6 mM of NaCl. Three trials were performed and within each each sample, three measurements were taken where each measurement consisted of 20 runs. The error bars represented standard deviation.

Transmission Electron Microscopy studies. The morphology of the protein•DNA complex and lipoproteoplex were studied using transmission electron microscopy (TEM). The complexes were formed as explained above and 3 μL of solution was applied on formvar carbon coated 400 mesh copper grids and incubated for 1 minute. The excess solution was blotted out and washed with 2×3 μL of $dH_2O$ and the sample was stained using 3 μL of 1% uranyl acetate solution for 1 minute and excess solution was blotted off. TEM was performed using Phillips CM-100 transmission electron microscope. The sizes of the complexes were measured using ImageJ.

Statistical Analysis. Statistics were computed for each experimental method to summarize the mean expression levels and associated standard deviations. A Student's t-test was used to compare different experimental conditions. In each statistical analysis, a p value less than 0.05 was considered significant.

Figure 8:
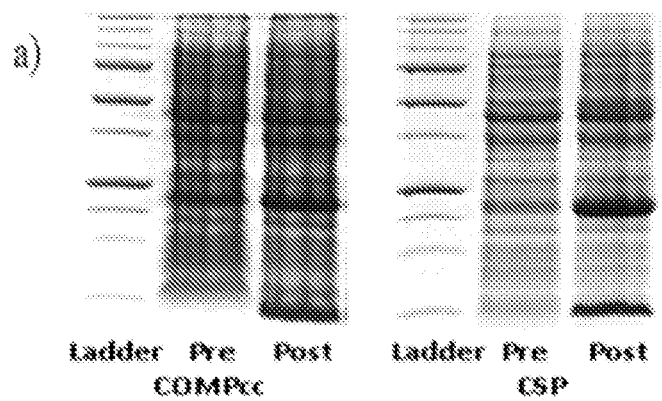
FIG. 8. a) Pre and post expression of COMPcc and CSP, b) Purified COMPcc, c) purified CSP. 1—Protein ladder, 2—cell lysate, 3—flow through, 4-10 elution fractions with 4-5—200 mM imidazole, 6-8—500 mM imidazole and 9-10—1 M imidazole.
Figure 8:
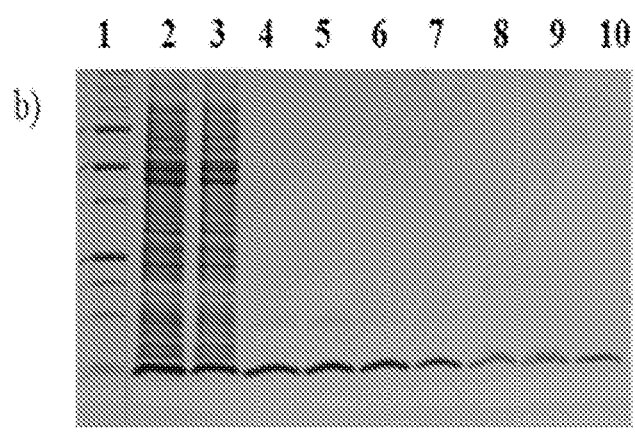
Figure 8:
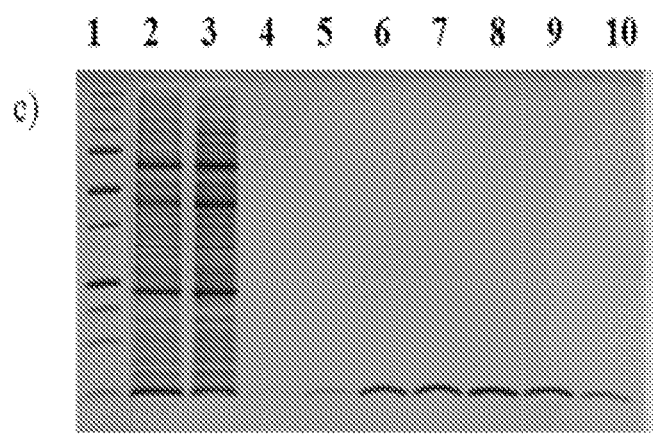

Results. Expression and purification of protein. The solvent exposed residues at b and c position of the heptad repeat of abcdefg of COMPcc were mutated into arginine by PCR assembly to generate the supercharged protein CSP (FIG. 1). Notably, CSP showed higher expression in E. coli relative to the parent COMPcc (FIG. 8a). While a specific purification protocol was developed to stabilize the highly charged (theoretical charge of +53) CSP, sufficient quantities of protein were produced (FIG. 8b, c).

Figure 2:
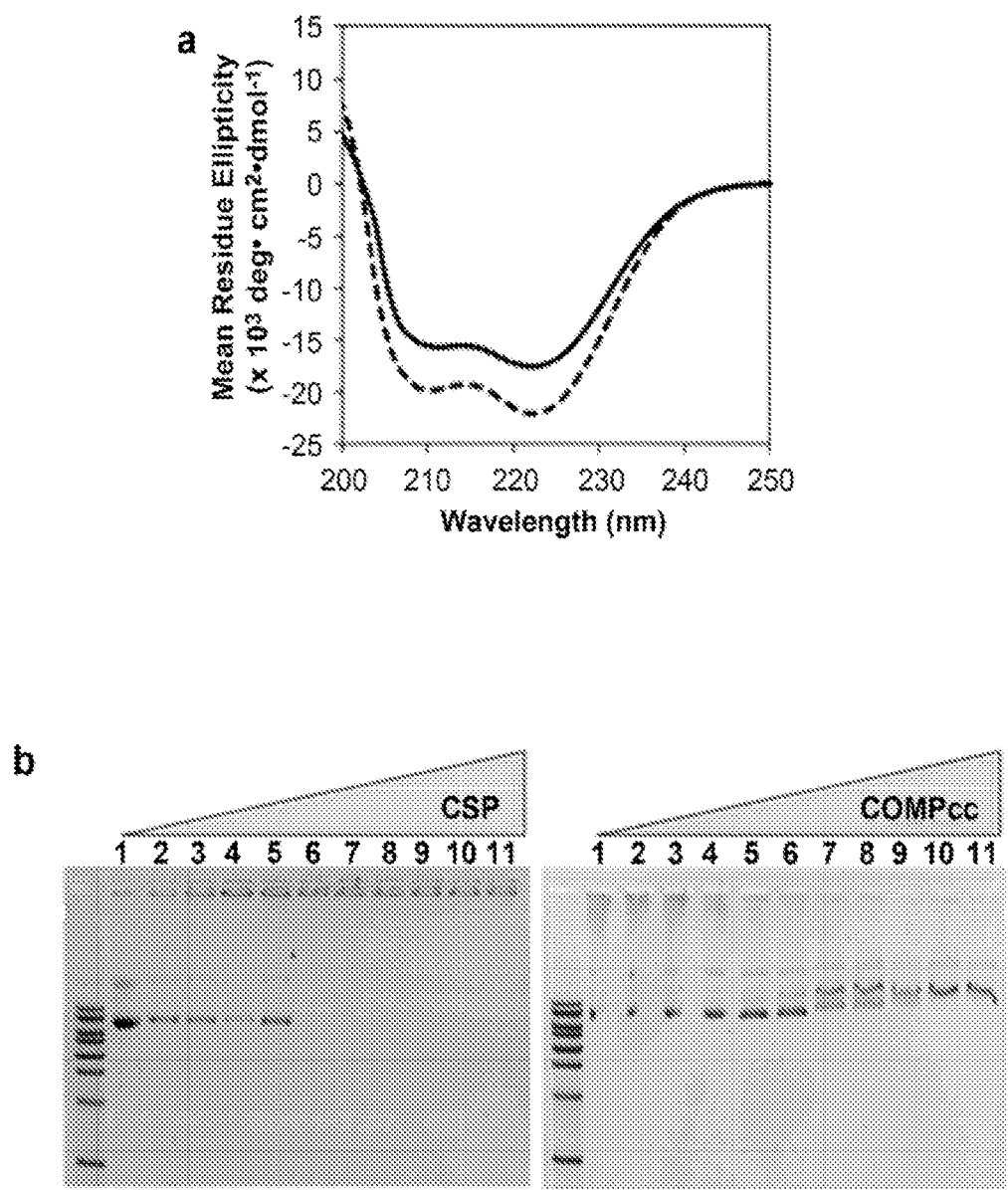
FIG. 2. In vitro studies on CSP and COMPcc. a) CD wavelengths scan of CSP (dashed line) and COMPcc (solid line) at 4° C. at 10 µM concentration. Scans represent an average of three trials. b) Plasmid DNA binding to protein with increasing w/w ratio evaluated through mobility shift assay on 1% agarose gel of CSP binding to DNA (left) and COMPcc binding to DNA (right). In both gels L-1 kb DNA ladder, 1-plasmid DNA alone. Proteoplexes prepared at different protein to DNA w/w ratio: 2-0.5:1, 3-1:1, 4-2:1, 5-3:1, 6-5:1, 7-8:1, 8-10:1, 9-13:1, 10-16:1, 11-18:1.
Figure 9:
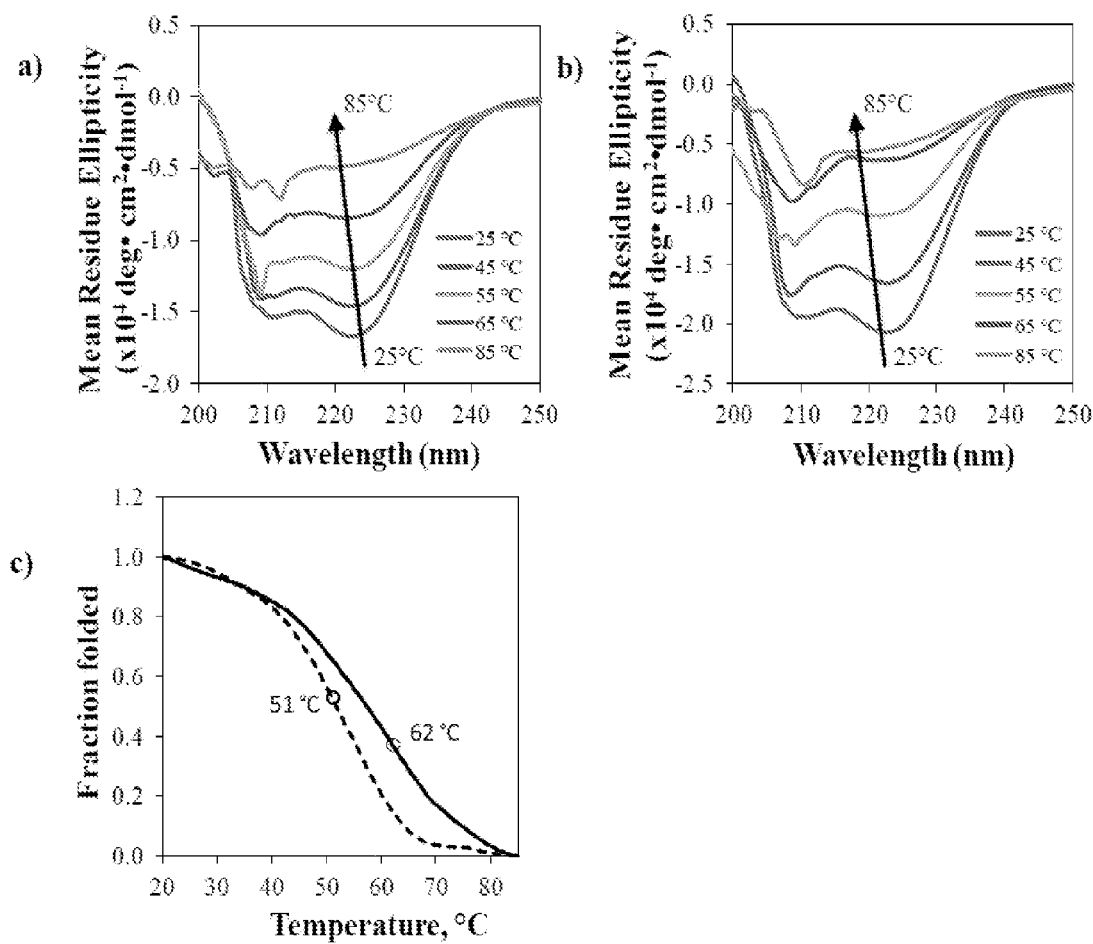
FIG. 9. Temperature wavelength scan of a) COMPcc and b) CSP; c) fraction folded of CSP and COMPcc.

Secondary structure studies. Circular dichroism (CD) spectroscopy was conducted on CSP and its parent COMPcc to assess the effects of arginine mutations on the secondary structure (FIG. 2a). Wavelength scans demonstrated that both CSP and COMPcc were indeed alpha-helical. Surprisingly, CSP exhibited enhanced helical structure when compared to the parent COMPcc (FIG. 2a). The supercharging did not negatively affect the structure; however, CSP exhibited a 10° C. decrease in the melting temperature ($T_m$) in comparison to the parent COMPcc (FIG. 9).

Optimization of plasmid DNA and protein binding ratio. The ability of CSP to complex plasmid DNA was evaluated by electrophoretic mobility shift assay on agarose gel (FIG. 2b). A fixed concentration of β-galactosidase plasmid DNA was mixed with varying amount of CSP or COMPcc at certain w/w ratios. The CSP, bearing a theoretical charge of +53 as a pentamer, exhibited efficient binding to plasmid DNA through non-covalent interactions with a complete shift at a protein to DNA w/w ratio of 5:1 (FIG. 2b). By contrast, COMPcc (theoretical charge −6) demonstrated a negligible DNA shift even at higher ratios of 18:1 (FIG. 2b), suggesting that the engineered positive charge indeed enabled DNA complexation.

Figure 3:
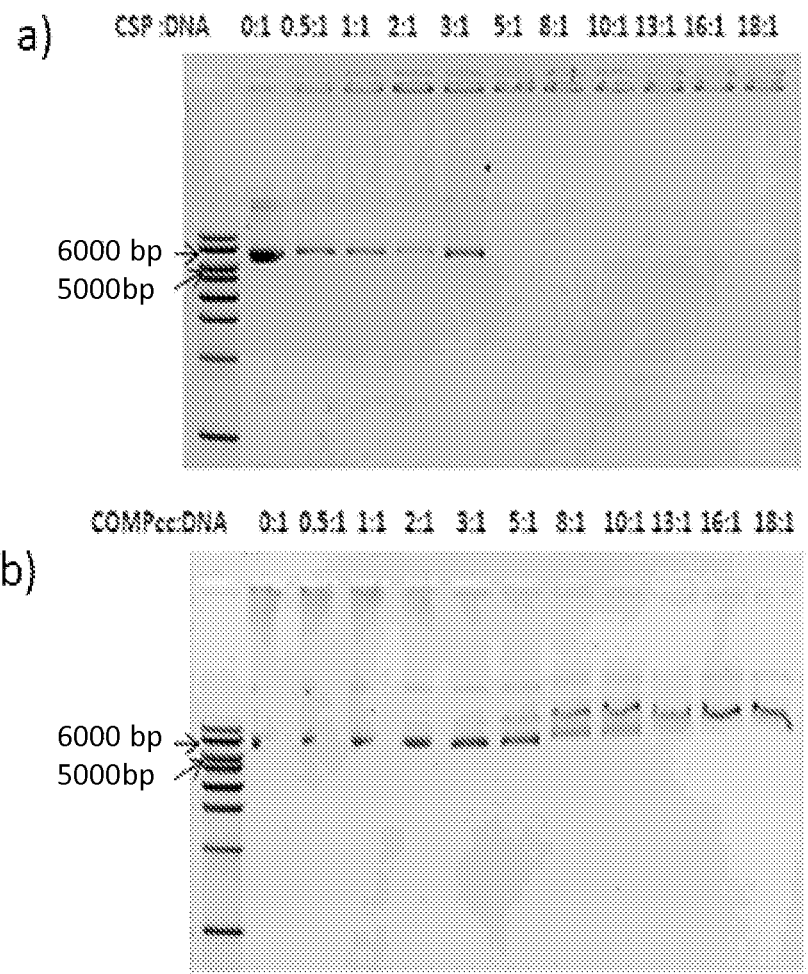
FIG. 3(a) shows the plasmid DNA binding evaluated through gel retardation assay.
FIG. 3(b) shows that COMPcc showed negligible DNA shift at higher ratios of 18:1.
FIG. 3(c) shows the β-galactosidase gene transfection across different cell lines in which MC3T3 and MCF7 shows drastic increase in transfection using CSP.
FIG. 3(d) shows the β-galactosidase gene transfection tested in the presence and absence of the proteins as well as the cationic lipid Fugene HD, X-tremeGENE and compared to the modified HIV-1 Tat peptide.
FIG. 3(e) shows a cytotoxicity study evaluated by use of a 3-(4,5-dimethylthiazol-2-yl)-2,5-diphenyl tetrasodium bromide, MTT assay.
Figure 3:
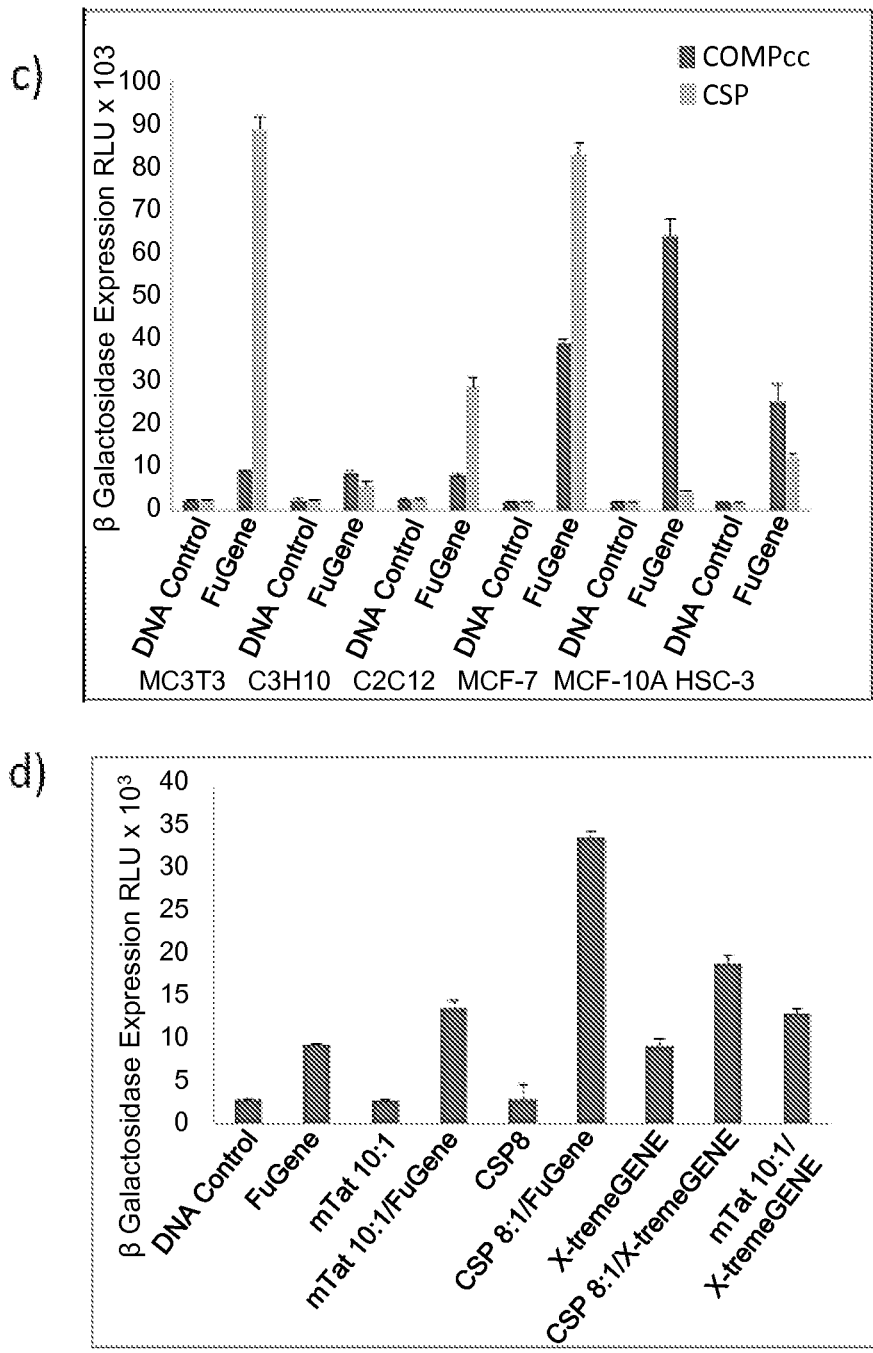
Figure 3:
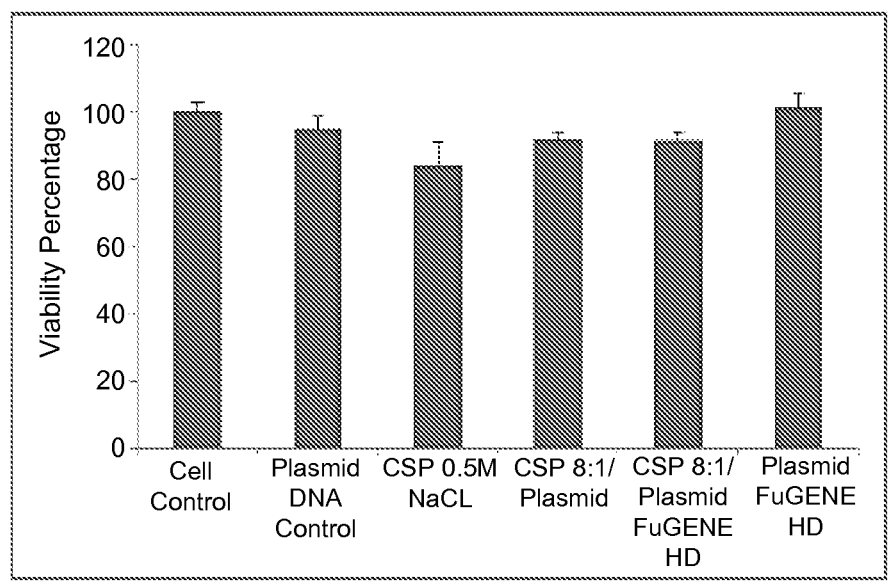

FIG. 3(a) shows the plasmid DNA binding evaluated through gel retardation assay, which exhibited that the CSP efficiently binds to plasmid DNA and demonstrated a complete shift at protein to DNA w/w ratio of 5:1, whereas as shown in FIG. 3(b) COMPcc showed negligible DNA shift at higher ratios of 18:1. FIG. 3(c) shows the β-galactosidase gene transfection across different cell lines in which MC3T3 and MCF7 shows drastic increase in transfection using CSP. FIG. 3(d) shows the β-galactosidase gene transfection tested in the presence and absence of the proteins as well as the cationic lipid Fugene HD, X-treme and compared to the modified HIV-1 Tat peptide. 25 Although the CSP alone was not able to transfect the DNA, a dramatic increase in transfection efficiency was observed in the presence of both CSP and FuGene HD. Also, the transfection efficiency of CSP-FuGene HD complex was higher compare to Tat-FuGene HD complex. FIG. 3(e) shows a cytotoxicity study evaluated by use of a 3-(4,5-dimethylthiazol-2-yl)-2,5-diphenyl tetrasodium bromide, MTT assay. The CSP alone and ternary complex as well is not cytotoxic to the cells.

Lipoproteoplex leads to enhanced transfection. To determine whether the lipoproteoplexes could indeed deliver DNA, the transfection of the β-galactosidase gene was assessed in presence and absence of the proteins plus cationic lipid, FG. As a control, DNA alone was treated with cells, yielding little evidence of transfection (FIG. 4a). FG in presence of DNA revealed a modest 3-fold increase in transfection relative to naked DNA. COMPcc•DNA(8:1)•FG demonstrated nearly similar transfection to FG•DNA (4:1) (FIG. 4a). Compared to the FG positive control, the ternary lipoproteoplex complex CSP•DNA(8:1)•FG outperformed it, with a 6-fold increase in transfection (FIG. 4a). The efficacy of the CSP lipoproteoplex was compared to a previously studied mTat•DNA(10:1)•FG mixture, yielding a 2.5 fold improved transfection. Notably, superior transfection efficiency was observed with CSP•DNA(8:1)•FG lipoproteoplex (FIG. 4b).

Figure 5:
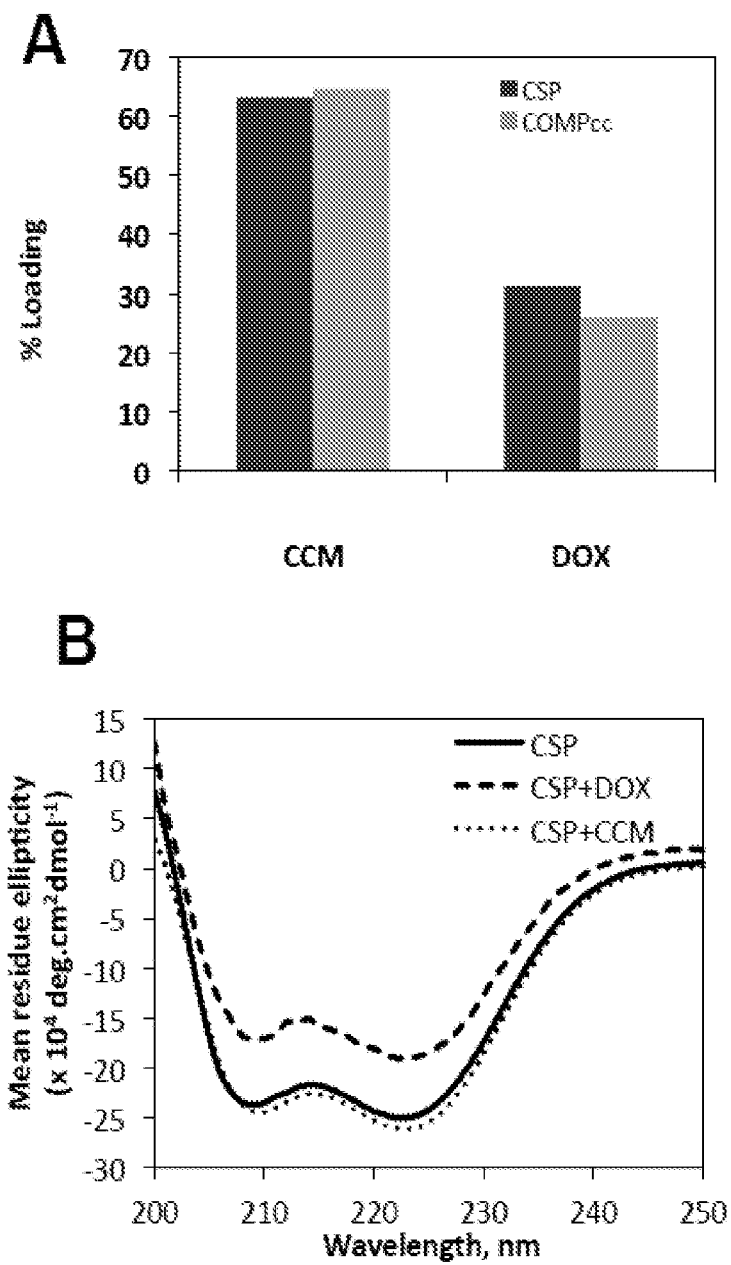
FIG. 5(a) shows that CSP and COMPcc showed effective binding to curcumin (CCM) with 63% and 64% loading respectively, while doxorubicin (DOX) loading was observed to be 31% and 26% respectively.
FIG. 5(b) shows the binding of DOX and CCM to CSP. The CCM bound CSP showed no change in secondary structure as compared to CSP alone, whereas the DOX binding exhibited a loss in helicity.
FIG. 5(c) show that COMPcc protein bound ccm and dox showed enhanced helical content as compared to COMPcc protein alone.
Figure 5:
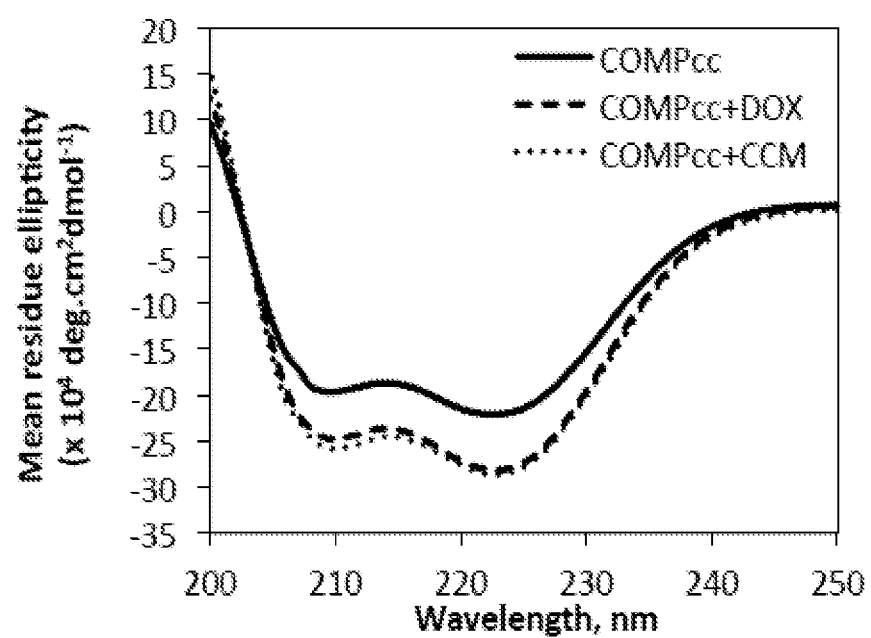

As shown in FIG. 5(a), CSP8 and C showed effective binding to curcumin (ccm) with 63% and 64% loading respectively, while doxorubicin (dox) loading was observed to be 31% and 26% respectively. The secondary structure of the CSP and COMPcc protein bound to ccm and dox was evaluated using CD immediately after separation of the free drug from the bound one. As shown in FIGS. 5(b) and 5(c), the addition of ccm to CSP8 showed no change in secondary structure as compared to CSP alone, whereas the dox binding exhibited a loss in helicity. However, as shown in FIGS. 5(d) and 5(e), COMPcc protein bound ccm and dox showed enhanced helical content as compared to COMPcc protein alone.

Figure 6:
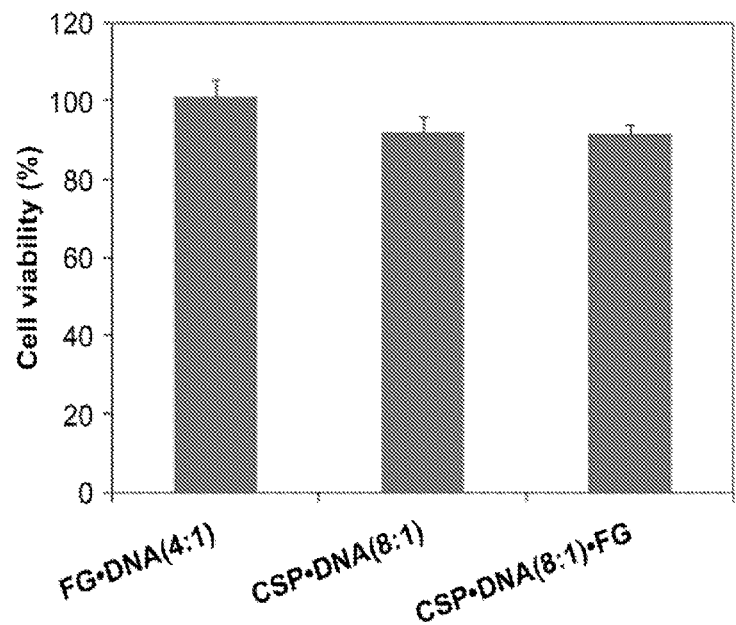
FIG. 6. Cell viability evaluated by MTT assay after treatment of CSP and FG complexed with plasmid DNA and liproteoplex complex with MC3T3-E1 cell. Data is shown as the mean±standard deviation obtained from quadruplicates and compared to the mean of control group. The control group consist of non-transfected cells (100% viability). No significant difference was observed between CSP•DNA(8:1) and FG•DNA(4:1) or CSP•DNA(8:1)•FG and FG•DNA(4:1) (p<0.05).

Cytotoxicity of lipoproteoplexes. Cellular viability was measured by the MTT assay of cells treated with the plasmid DNA complexed with CSP and FG. The proteoplex of CSP•DNA(8:1)•FG illustrated 91.8±4.3% cell viability. The ternary lipoproteoplex also showed similar cell viability (91.6±2.26%) to the CSP•DNA(8:1) treatment. All of the constructs were essentially non-toxic in which no significant difference was observed between CSP•DNA(8:1) and FG•DNA(4:1) or CSP•DNA(8:1)•FG and FG•DNA(4:1) ($p<0.05$) (FIG. 6).

Figure 10:
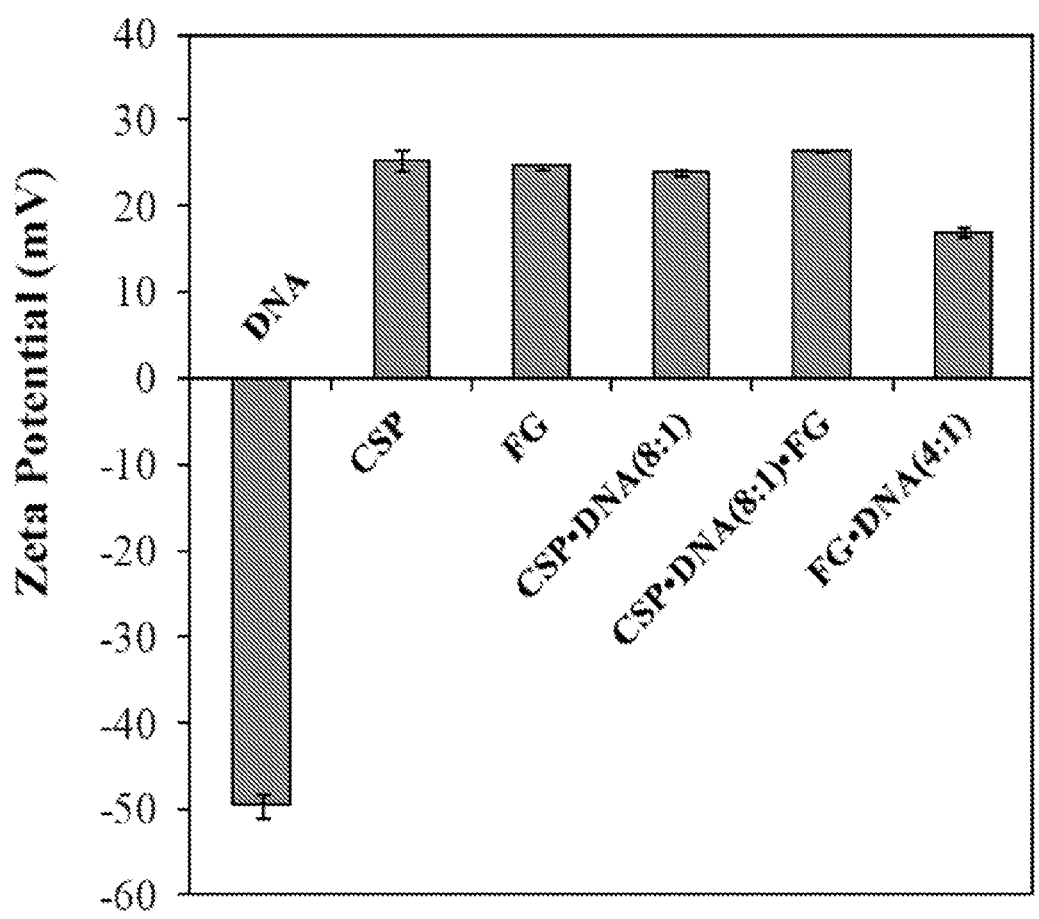
FIG. 10. Zeta potential of plasmid DNA, CSP and FG alone and the respective complexes and a lipoproteoplex. The data represents the average of three individual trials with mean std. deviation.

Surface properties and morphology of complexes. To assess the surface characteristics of the proteins, proteoplexes and lipoproteoplexes, the surface charge of the individual components and complexes were determined via zeta potential measurements. As expected, plasmid DNA revealed a negative zeta potential of −49.70±1.28 mV, while CSP alone was positive with a value of +25.51±1.28 mV (Table 1, FIG. 10). The CSP•DNA(8:1) complex exhibited a slightly less positive zeta potential relative to CSP alone with a value of +24.00±0.27 mV; with the addition of FG, the zeta potential did not change significantly, demonstrated by the value of +26.58±0.10 mV (Table 1, FIG. 10). FG alone possessed a positive zeta potential of +24.83±0.27 mV; after mixing it with negatively charge DNA, the zeta potential significantly decreased to +17.17±0.68 mV (Table 1, FIG. 10).

TEM analysis was performed for the CSP•DNA(8:1), FG•DNA(4:1) and the ternary lipoproteoplex complex. At 8:1 w/w ratio, the CSP•DNA(8:1) showed aggregate structures with an average Feret diameter of 270.4±84.7 nm (FIG. 7a, FIG. 11 (Table 2)). A drastic change in shape, size and overall morphology of the complex was observed in presence of FG; the FG•DNA(4:1) and CSP•DNA (8:1)•FG showed small spherical particles with a Feret diameter of 354.8±58.4 nm and 317±47 nm, respectively (FIG. 7b, c, FIG. 11 (Table 2)).

TABLE 1

Zeta potential measurements.
Zeta potential (mV)[a]

| | |
|---|---|
| DNA | −49.70 ± .28 |
| CSP | +25.51 ± 1.28 |
| FG | +24.83 ± 0.27 |
| CSP•DNA | +25.00 ± 0.36 |
| CSP•DNA•FG | +26.58 ± 0.10 |
| DNA•FG | +17.17 ± 0.68 |

Figure 4:
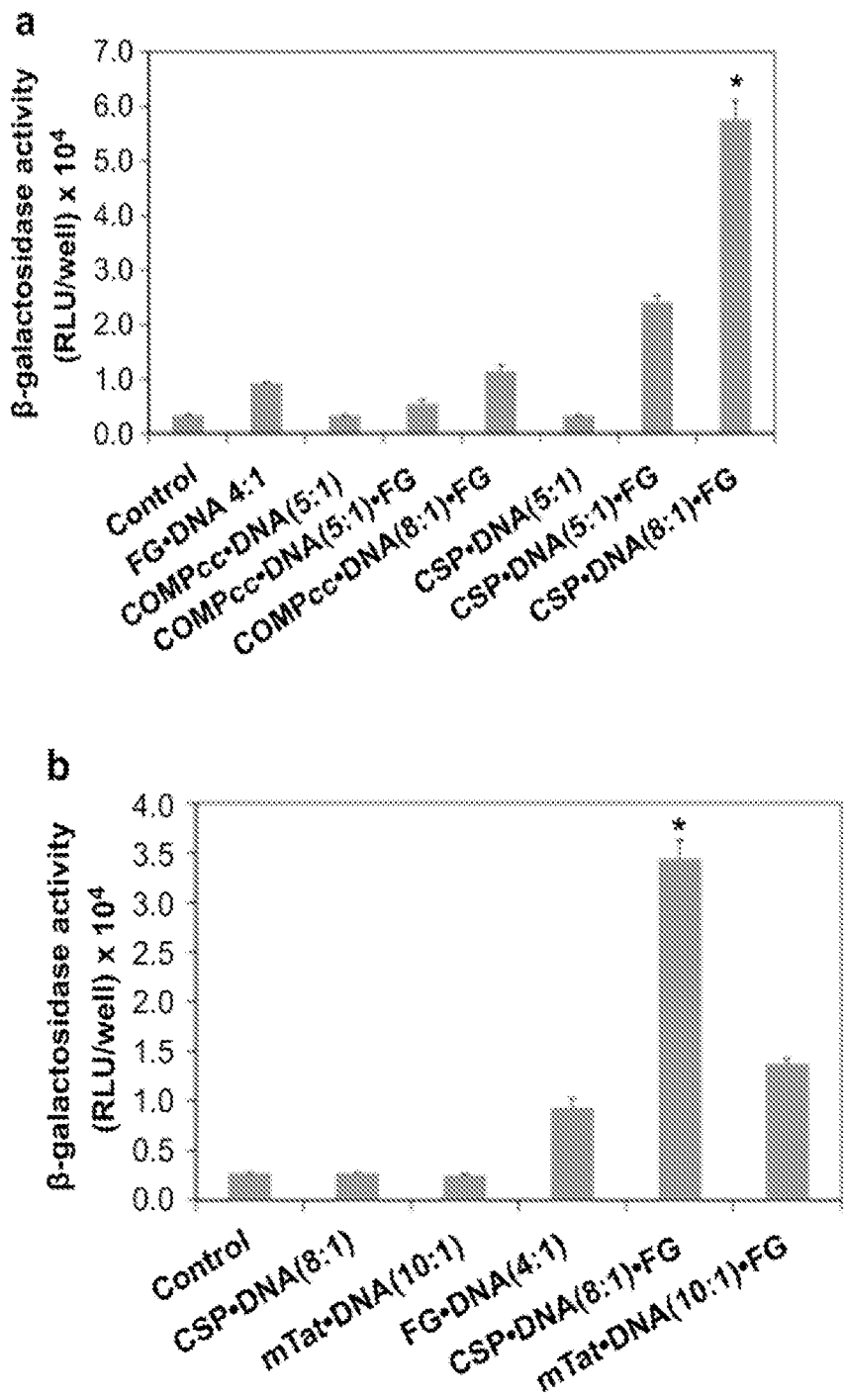
FIG. 4. Another representation of in vitro transfection efficiency for β-galactosidase DNA. FG•DNA(4:1), COMPcc•DNA (5:1), COMPcc•DNA(5 or 8:1)•FG, CSP•DNA(5:1), CSP•DNA(5 or 8:1)•FG, mTat•DNA(10:1) and mTat•DNA(10:1)•FG. a) * indicates p<0.0001, comparison of control (DNA only), FG•DNA(4:1) etc, b)* indicates p<0.0001 comparison of control (DNA only), CSP•DNA(8:1) etc. Data represents the mean β-galactosidase activity (relative light units, RLU)/well with a standard deviation obtained from quadruplicates.

We have developed lipoproteoplexes comprised of an engineered CSP for effective condensation of negatively charged DNA in conjunction with cationic lipid, FG, for enhanced gene delivery. While supercharging the protein did not negatively affect its structure, CSP exhibited a 10° C. decrease in the melting temperature ($T_m$) in comparison to the parent COMPcc (FIGS. 2a, 9). The COMPcc, which possessed a more negatively charged surface, demonstrated poor binding ability to plasmid DNA, while CSP exhibited a pronounced positively charged surface that bound plasmid DNA at lower w/w ratio as confirmed by electrophoretic mobility shift assay (FIG. 2b). The in vitro transfection studies showed that the CSP with cationic lipid, FG, significantly enhanced the transfection relative to FG and CSP alone. More importantly, it outperformed another cell penetrating peptide mTat as shown via a significant increase in β-galactosidase activity (FIG. 4).

Although many cationic polymer and cationic lipid-based systems have been developed for enhanced transfection, cytotoxicity is always a major concern for in vitro and in vivo studies. Our cell viability assay on MC3T3-E1 cells show that the CSP•DNA(8:1) with or without FG did not contribute any significant cytotoxic effect when compared to FG•DNA(4:1) (FIG. 6). Although cell viability is compromised to a minimal extent with the lipoproteoplex as compared to the FG•DNA(4:1), it demonstrates a significant increase in transfection.

Figure 7:
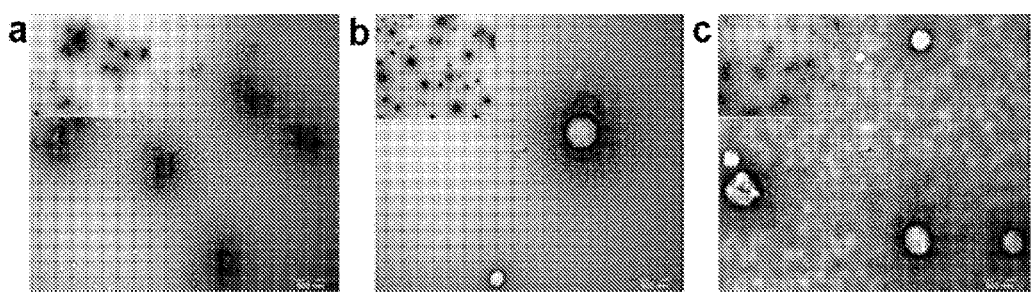
FIG. 7. TEM images of different complexes a) CSP•DNA (8:1), b) FG•DNA(4:1), c) CSP•DNA(8:1)•FG. The scale bars in the image is 500 nm and the insets has 2 µm.

The zeta potential studies demonstrate that CSP has better DNA condensation ability relative to FG alone as CSP•DNA (8:1) reveals a more positive zeta potential than the FG•DNA(4:1) complex (Table 1). Although the condensation of ability of CSP is higher than FG, the particles are polydisperse with irregular size as supported by literature. By contrast, both FG•DNA(4:1) and CSP•DNA(8:1)•FG complex exhibit spherical particles (FIG. 7). For effective gene delivery, the particle size is critical and the ternary lipoproteoplex reveals a more uniform particle size leading to enhanced transfection.

The increase in the transfection efficiency of the lipid component in the presence of CSP was observed to be synergistic and was surprising and unexpected.

EXAMPLE 2

Figure 12:
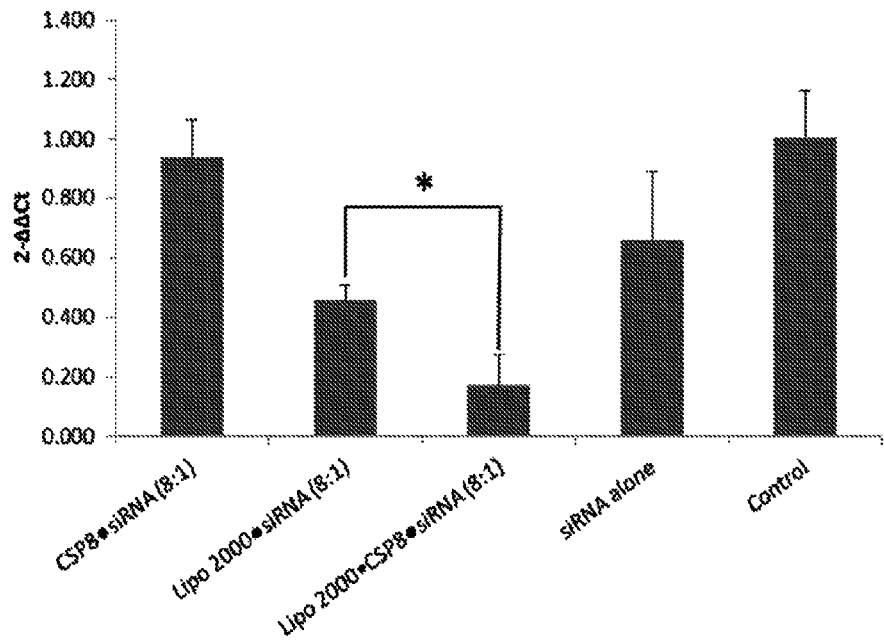
FIG. 12: in vitro GAPDH siRNA transfection of MC3T3 E1 cells with CSP8•siRNA (w/w 8:1), Lipofectamine 2000•siRNA (w/w 8:1), Lipofectamine 2000•CSP8•siRNA (w/w 8:1), siRNA alone, negative control (untreated cells). Lipofectamine2000•siRNA was prepared according to the manufacturer's instructions (Life Technologies). Quantitative real-time PCR data is represented by the comparative Ct (critical threshold) method. * indicated a p value<0.05.

This example provides further description of use of the present complexes in delivery of nucleic acids to cells. Results are shown in FIG. 12 at p value>0.005. For siRNA transfections, MC3T3 E1 cells were seeded in a 96-well plate at a density of $5 \times 10^3$ cells/well in the same media conditions as described above. CSP•GAPDH siRNA (Invitrogen) complexes were formed at a w/w 8:1 ratio for 30 minutes at room temperature. After preparation of cells for this assay, the media was aspirated from the 96-well plate and washed with phosphate buffered saline pH 7.4. Serum-free alpha-MEM was then added to the protein•siRNA complex (to a total volume of 50 μL) for transfer to the newly washed cells. When Lipofectamine 2000 was used, a 1 μg/μL solution of this transfection reagent was mixed with the protein•siRNA complex. After adding the transfection reagent, the mixture was placed on a rotator for 15 minutes prior to adding the entire 50 μL mixture to the appropriate wells. These cells were left to incubate for 4 hours at 37° C., 5% $CO_2$. Following the incubation period, the medium was aspirated, washed three times with phosphate buffered saline pH 7.4 and replaced with alpha-MEM medium containing 10% FBS and 1% penicillin. The cells were incubated at 37° C., 5% $CO_2$ for 48 hours. After 48 hours, the cells were aspirated of medium and subjected to 100 μL of lysis buffer. RNA was isolated using an RNeasy Extraction kit (Qiagen), and total concentrations were determined using a Nanodrop 2000 UV/VIS spectrophotometer at 260 nm for subsequent cDNA synthesis using a Quantitect Reverse Transcriptase kit (Qiagen). The concentration of cDNA was determined using the aforementioned Nanodrop 2000 at 260 nm for normalizing total cDNA weights in the subsequent real-time PCR (Rotor-Gene SYBR Green PCR® Kit, Qiagen). The final concentration of cDNA used for real-time PCR was 100 ng as per the manufacturer's recommendations. The primer sequences for PCR are as follows: GAPDH Forward, 5'-TCCACGACATACTCAGCAC-3' (SEQ ID NO:8) and GAPDH Reverse, 5'-AACGACCCCTTCATTGAC-3' (SEQ ID NO:9). Quantitative PCR (qPCR) data was analyzed by the comparative $C_T$ (critical threshold) method.

Figure 13:
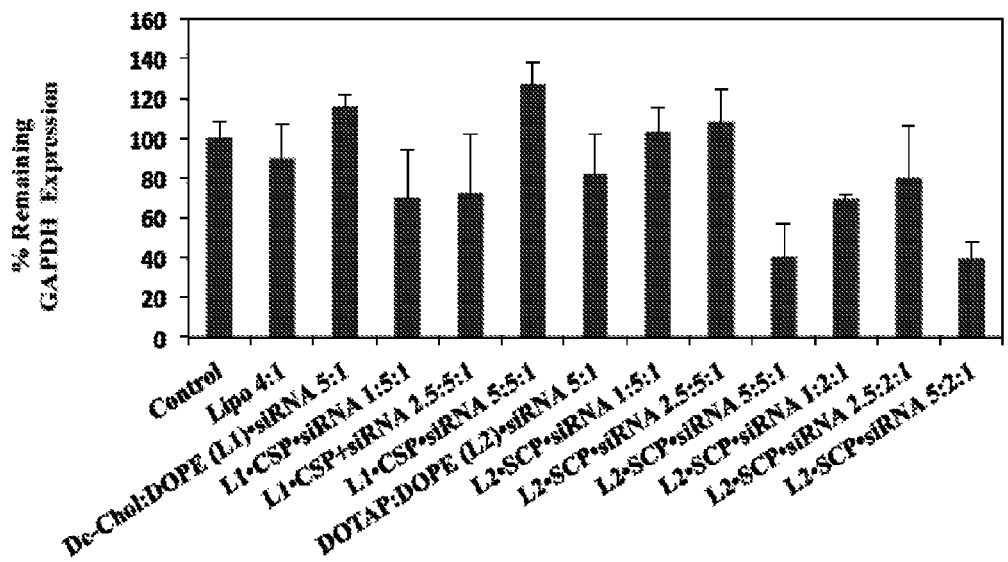
FIG. 13. In vitro GAPDH siRNA transfection in MC3T3 E1 cells with different composition of Dc-Cholesterol: DOPE and DOTAP:DOPE lipids with CSP and siRNA. The suppression of GAPDH was confirmed by determining the activity using KDalert™ kit (Life technologies).

In another study, the efficiency of GAPDH siRNA transfections in a MC3T3 E1 cells was studied by determining the residual GAPDH activity in the cells. The MC3T3 E1 cells were seeded in a 96-well plate at a density of $5 \times 10^3$ cells/well in the same media conditions as described above. CSP•GAPDH siRNA (Invitrogen) complexes were formed at a different w/w ratio for 30 minutes at room temperature and then the preformed DOTAP:DOPE liposomes were added at different w/w ratio and incubated for another 15 minutes. After preparation of cells for this assay, the media was aspirated from the 96-well plate and washed with phosphate buffered saline pH 7.4 and 100 μL of serum-free alpha-MEM media was added. The complexes (total volume of 10 μL with respective siRNA concentration) was added to each well in quadruplicate. When Lipofectamine 2000 was used, a 1 μg/μL solution of this transfection reagent was mixed with the protein•siRNA complex. After adding the transfection reagent, the mixture was placed on a rotator for 15 minutes prior to adding the entire mixture to the appropriate wells. These cells were left to incubate for 4 hours at 37 Deg C, 5% $CO_2$. Following the incubation period, the medium was aspirated, washed three times with phosphate buffered saline pH 7.4 and replaced with alpha-MEM medium containing 10% FBS and 1% penicillin. The cells were incubated at 37 Deg C, 5% $CO_2$ for 48 hours. The cells were washed with phosphate buffer saline pH 7.4 and lysed using the buffer provided in KDalert GAPDH activity kit. The GAPDH suppression was analyzed by the protocol provide by the manufacturer (Life technologies) the results of which are shown in FIG. 13. The sizes of the complexes was studied using dynamic light scattering.

Figure 14:
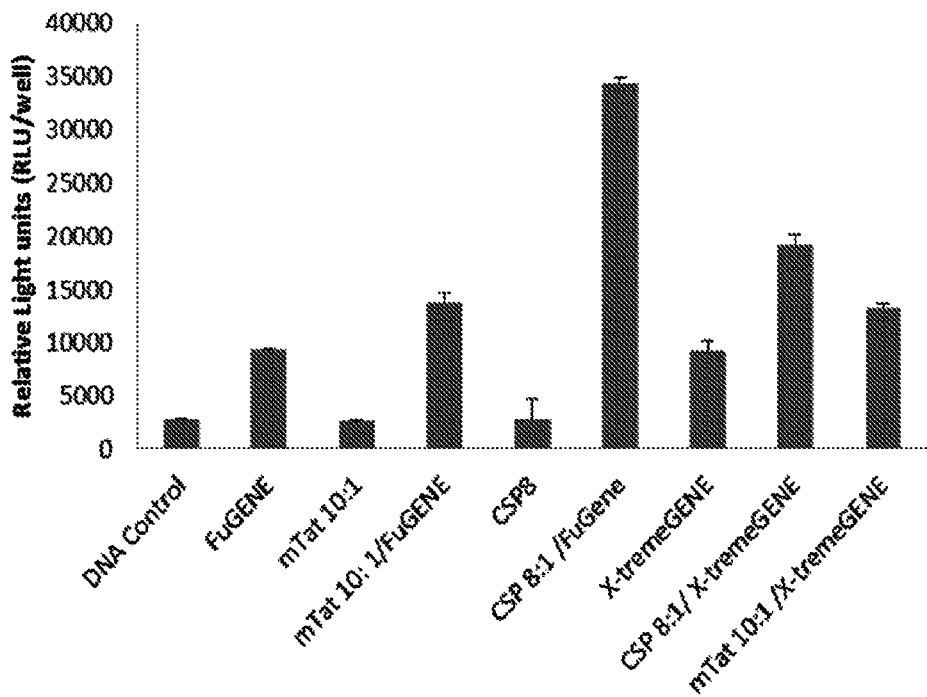
FIG. 14. In vitro transfection efficiency for β-galactosidase DNA. Negative control (untreated cells), FuGENE•DNA (4:1), mTat•DNA (10:1), CSP•DNA (8:1), FuGENE•CSP•DNA (8:1), X-tremeGENE•DNA (4:1), X-tremeGENE•CSP•DNA (8:1), X-tremeGENE•mTat•DNA (10:1). When lipoproteoplexes were formed, the w/w ratio of either FuGENE (Promega) or X-tremeGENE (Roche) and DNA was calculated according to the manufacturers instructions. Data represents the mean β-galactosidase activity (relative light units, RLU)/well with a standard deviation obtained from quadruplicates.

In another example, mTat—Modified Tat peptide used by Seiichi Yamano et al, 2011, Journal of controlled release 152, 278-285. was used. CSP was incubated with plasmid DNA (8:1 ratio), then mixed with either FuGENE (Promega) or X-tremeGENE (Roche). Results are shown in FIG. 14.

Figure 15:
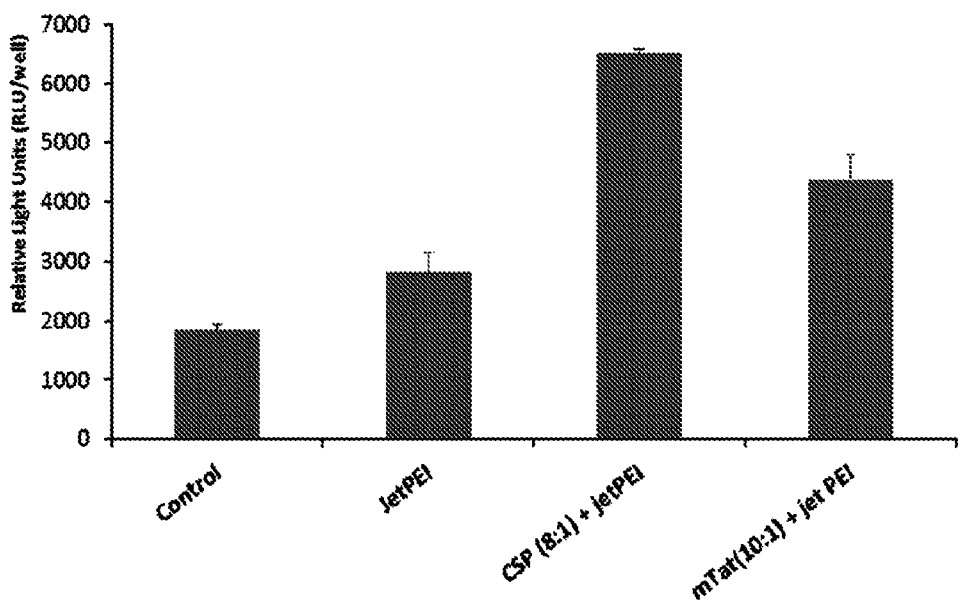
FIG. 15. In vitro transfection efficiency for β-galactosidase DNA. jetPEI•DNA(8:1), jetPEI•CSP•DNA (8:1), jetPEI•mTat•DNA(10:1)•FG, negative control (untreated cells). jetPEI•DNA was prepared according to the manufacturers instructions (Polyplus). Data represents the mean β-galactosidase activity (relative light units, RLU)/well with a standard deviation obtained from quadruplicates.

An example of CSP incubated with plasmid DNA (8:1 ratio), then mixed with jetPEI (Polyplus) is shown in FIG. 15.

Figure 16:
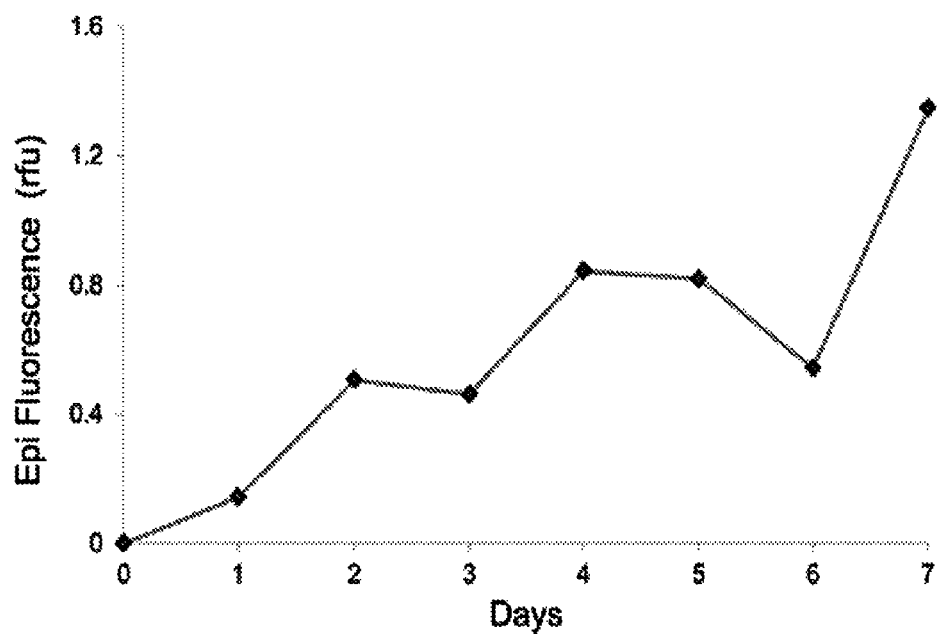
FIG. 16. In vitro siRNA release assay. A DOTAP/ DOPE•CSP•siRNA (5:5:1) lipoproteoplex was prepared with 500 pmol fluorescently labeled siRNA (siGLO, Thermo Fisher) and subsequently mixed with 10% hydrogel (Carbopol). The hydrogel was applied to a Franz diffusion cell with released aliquots extracted daily for 7 days from the reservoir pool for fluorescence measurements.

In vitro siRNA release assay performed with a Franz Diffusion cell is shown in FIG. 16. 500 pmol Fluorescently labeled siRNA (siGLO, Thermo Fisher) was used. The lipids were (DOTAP/DOPE+CSP)/siGlo (w/w/w 5:5:1). CSP mixed with cationic/neutral lipids first, then mixed with siGLO. Formed Lipoproteoplex then mixed with 10% hydrogel (Carbopol). The hydrogel was applied to a Franz Diffusion cell with aliquots taken at time points over a day period. The release profile is shown over 7 day period in FIG. 16.

Figure 17:
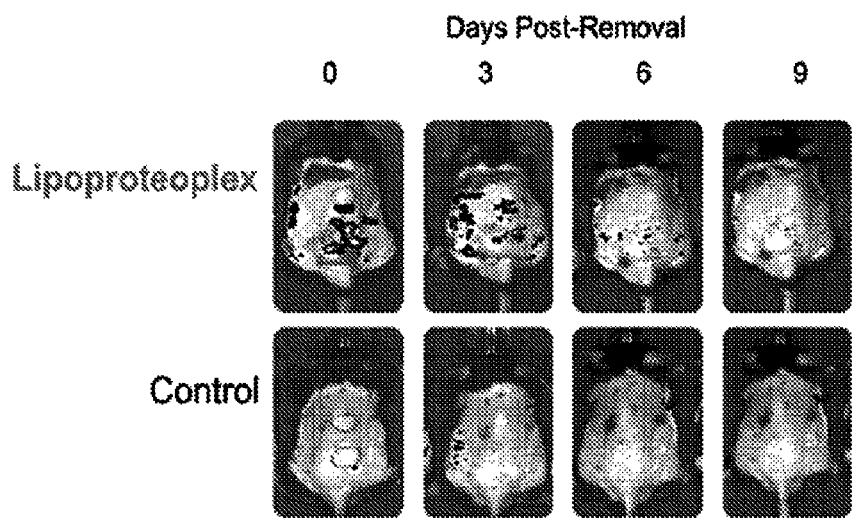
FIG. 17. Dermal Bioavailability Assay. A DOTAP/ DOPE•CSP•siRNA (5:5:1) lipoproteoplex was prepared with 500 pmol fluorescently labeled siRNA (siGLO, Thermo Fisher) and subsequently mixed with 10% hydrogel (Carbopol) prior to application to a 10 mm diameter area on intact dorsal skin of adult 8-12 week C57 mice. 3 days following application, the hydrogel was removed and the epi-fluorescence imaged using an in vivo imaging system (IVIS) Spectrum. A hydrogel bearing siGLO only was used a control.
Figure 18:
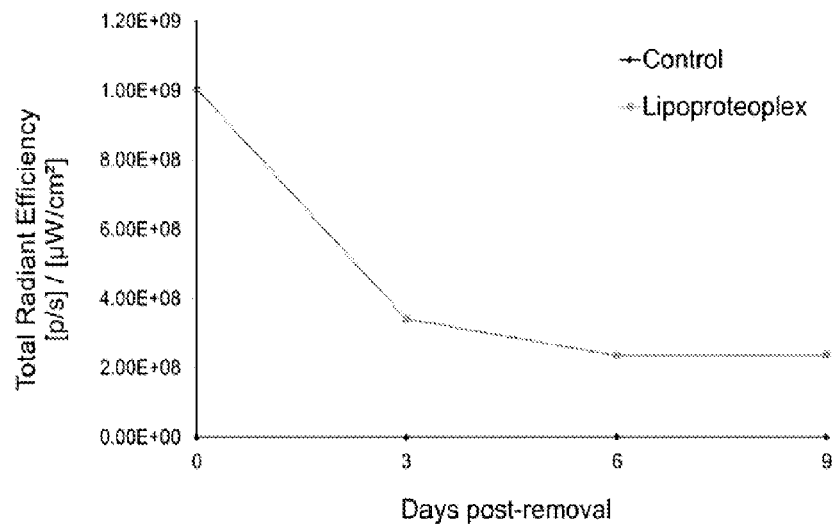
FIG. 18. Dermal Bioavailability Assay. Graphical representation of the available siGLO as described above as a function of time FIG. 19. Dermal Penetration Assay. A DOTAP/DOPE•CSP•siRNA (5:5:1) lipoproteoplex was prepared with 500 pmol fluorescently labeled siRNA (siGLO, Thermo Fisher) and subsequently mixed with 10% hydrogel (Carbopol) prior to application to a 10 mm diameter area on intact dorsal skin of adult 8-12 week C57 mice. At 0, 3, 5, 7, 10 and 14 days post-application, the hydrogel was removed and the underlying 10 mm skin biopsied. The skin biopsies were fixed overnight in 4% PFA, then cryopreserved in 20% sucrose/PBS, and embedded in OCT. 10 μm sections were used to detect fluorescence in mouse skin. DAPI was used to counterstain the nuclear region of the tissues.

Dermal Bioavailability Assay. Lipoproteoplex with fluorescently labeled siRNA (siGLO) was prepared as described above and mixed with 10% hydrogel (Carbopol). The hydrogel was applied to a 10 mm diameter area of intact dorsal skin of adult 8-12 week C57 mice in duoderm wells secured with tegaderm and surgical tape. After 3 days, dressing was removed followed by IVIS (In vivo imaging systems) analysis. The image is shown in FIG. 17 and the graphical representation is shown in FIG. 18.

Figure 19:
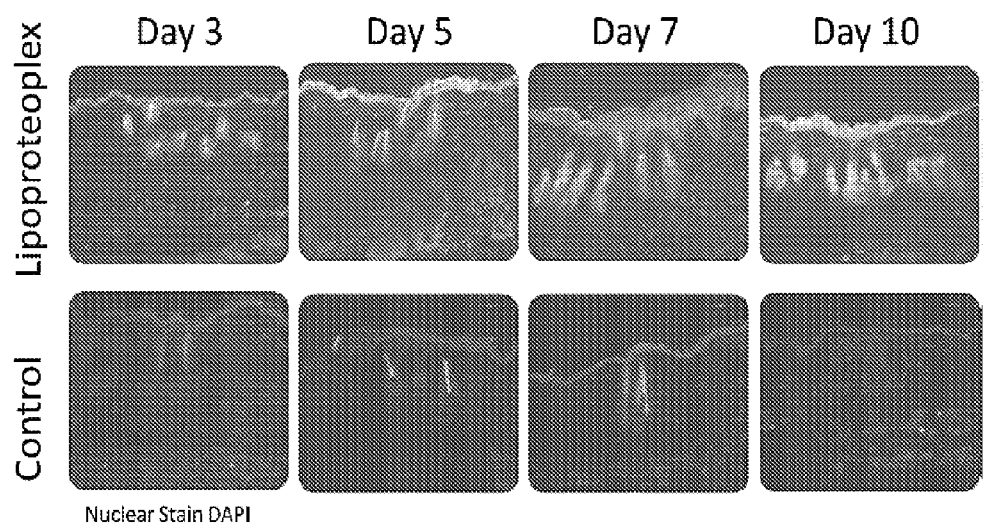
Figure 20:
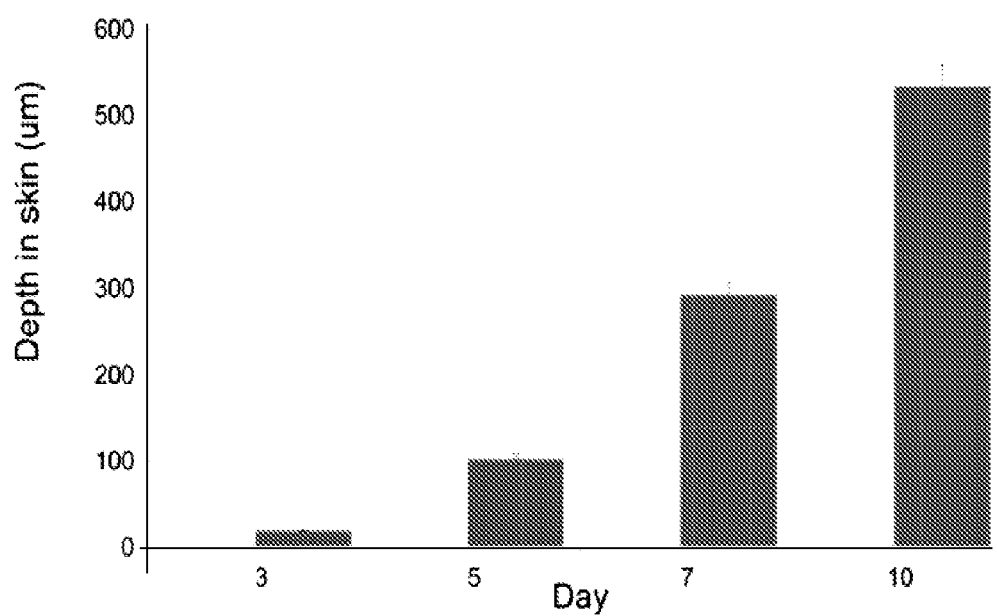
FIG. 20. Dermal Penetration Assay. Graphical Representation of the penetrated siGLO as described above as a function of time.

Dermal Penetration Assay. The hydrogel was prepared as described above and applied to a 10 mm diameter area of intact dorsal skin of adult 8-12 week C57 mice in duoderm wells secured with tegaderm and surgical tape. At 0, 3, 5, 7, 10 and 14 days post-application, the hydrogel was removed and the underlying 10 mm skin biopsied. The skin biopsies were fixed overnight in 4% PFA, then cryopreserved in 20% sucrose/PBS, and embedded in OCT. 10 um sections were used to detect fluorescence in mouse skin. DAPI was used to counterstain the tissues. Results are shown in FIG. 19. FIG. 20 provides a Graphical quantificative representation of the lipoproteoplex dermal penetration experiment. Lipoproteoplex reaches a peak depth at day 10.

Figure 21:
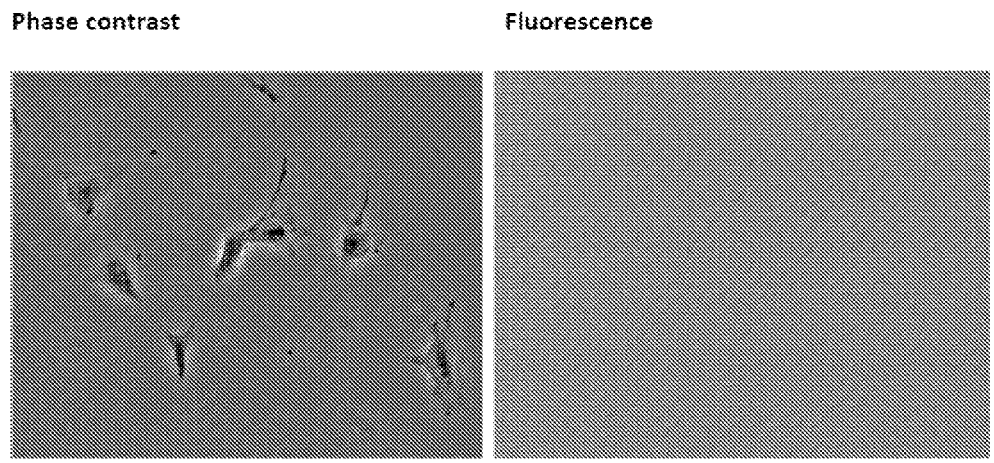
FIG. 21. The delivery of siRNA, as well as a small molecule curcumin using CSP and DOTAP:DOPE liposomes was confirmed by transfecting MC3T3 E1 cells and fluorescence microscopy imaging. Phase contrast images are to the left and fluorescence images are to the right. A is control; B is siRNA only; C is DOTAP:DOPE+siRNA; D is CSP+siRNA; E is DOTAP:DOPE+CSP+siRNA; F is DOTAP:DOPE+CSP+siRNA.
Figure 21:
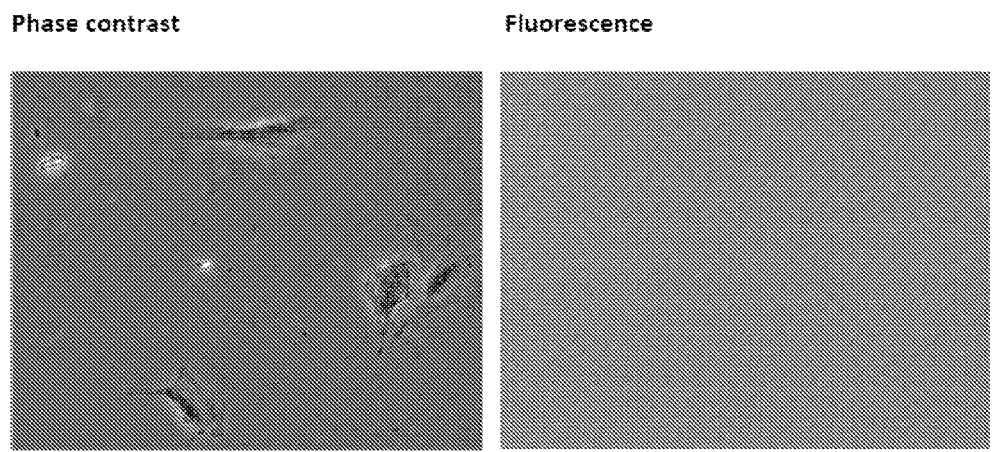
Figure 21:
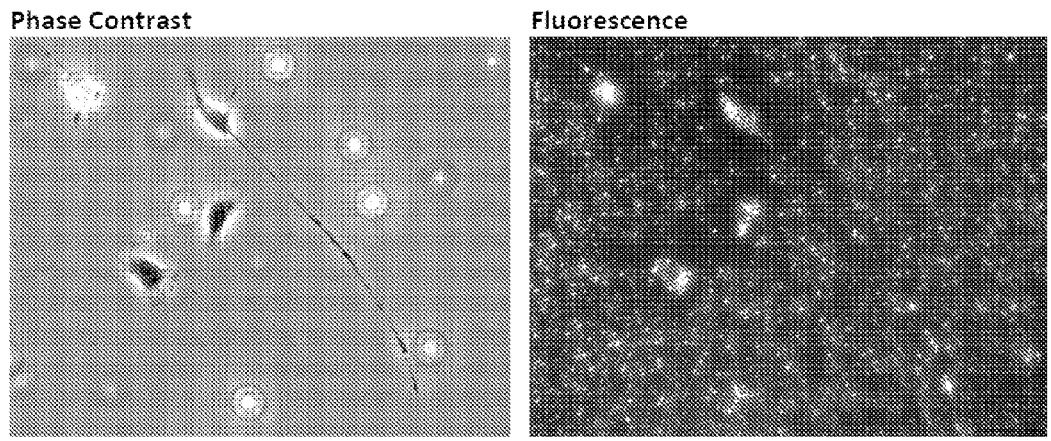
Figure 21:
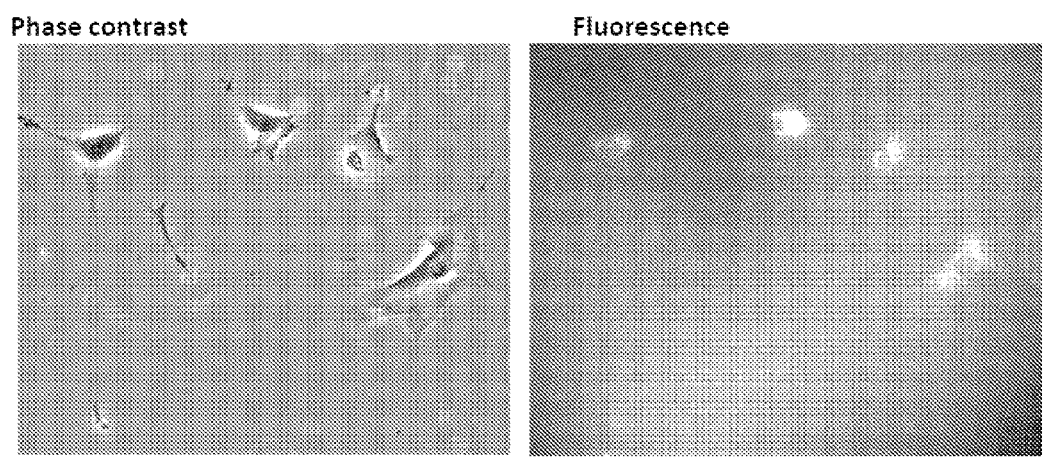
Figure 21:
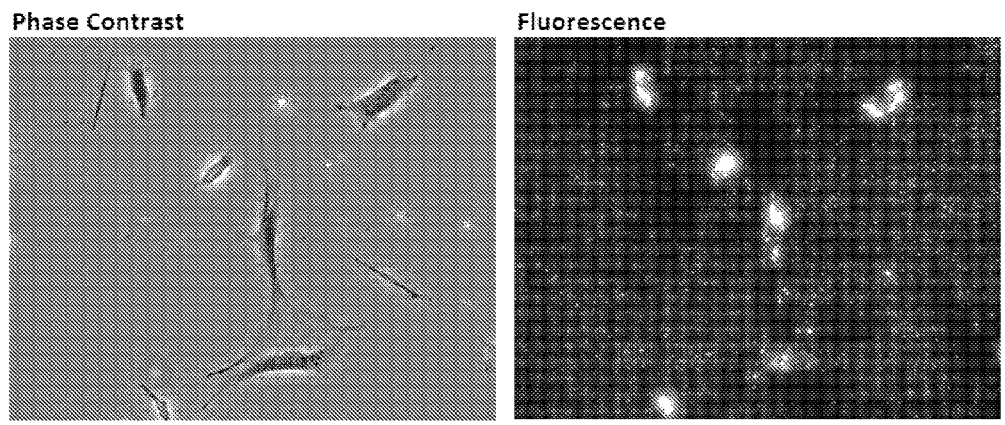
Figure 21:
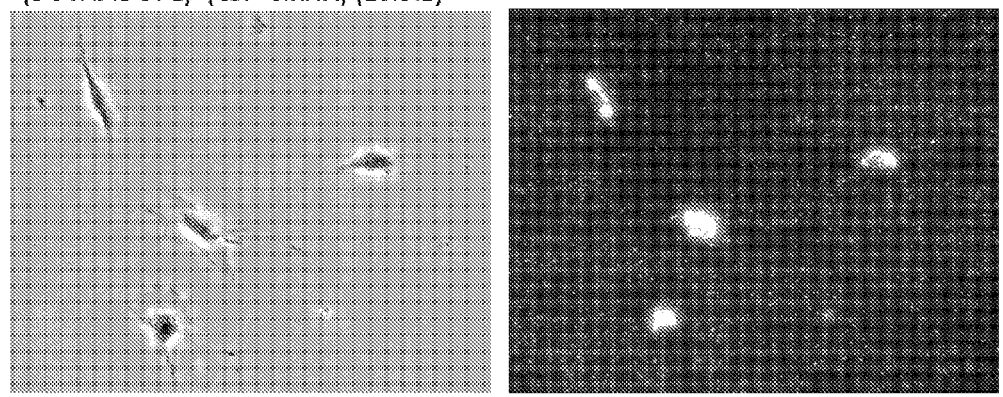

Dual delivery of Cy3-conjugated GAPDH siRNA and curcumin was studied by transfecting them using CSP and DOTAP:DOPE liposome based lipoproteoplexes. The internalization of the complex was observed using fluorescence microscope. The MC3T3 E1 cells were seeded in a 6-well plate with glass cover slip at the bottom of the plate at a density of $5\times10^4$ cells/well for 24 hrs in the same media conditions as described above. The complexes were formed as described above. After preparation of cells for this assay, the media was aspirated from the 6-well plate and washed with phosphate buffered saline pH 7.4 and 1 mL of serum-free alpha-MEM media was added. The complexes were added to each well and incubated for 4 hrs at 37 Deg C, 5% $CO_2$. Following the incubation period, the medium was aspirated, washed three times with phosphate buffered saline pH 7.4 and replaced with DMEM medium without FBS, penicillin and indicator dye to avoid the background fluorescence during the microscopy imaging. The glass cover slip was removed from the well and flip over the glass slide for live cell imaging using Nikon fluorescence microscope. The fluorescence from curcumin was observed under yellow green filter and for Cy3-siRNA a red filter was used. Also the cells were visualized under phase contrast mode. Results are shown in FIG. 21. As shown in FIGS. 21C and 21D, colocalization of cy3-conjugated GAPDH siRNA with the cell cytoplasim indicates uptake of lipoproteoplex.

Size of the complex, DLS studies were performed on siRNA and CSP, liposome complexes using Zetasizer Nano ZS90 (Malvern Instruments, UK) with a laser source of 630 nm. All the complexes were prepared with final siRNA concentration was kept at 1.84 ng/μL and the CSP was kept at 5 times and liposome at 10 time higher w/w concentration as that of siRNA. The complexes were prepared as explained above. All samples were diluted with 0.22 μm filter $dH_2O$. For CSP bound curcumin sample, 50 μM of CSP was incubated with 100 μM curcumin and incubated for 2 hrs and then this complex was used for binding to siRNA and liposomes.

TABLE 2

| Sample | Size (nm) |
| --- | --- |
| CSP•siRNA | 489.2 ± 17.4 |
| Liposome•siRNA | 196.4 ± 1.6 |
| CSP•siRNA•Liposome | 239.1 ± 4.9 |
| (CSP + Curcumin)•siRNA | 326.4 ± 19.3 |
| (CSP + Curcumin)•siRNA•Liposomes | 213.5 ± 6.1 |

It will be appreciated by persons of ordinary skill in the art that the present disclosure is not limited by what has been particularly shown and described herein. Rather, the foregoing detailed description of the specific embodiments and the appended figures have been presented only for illustrative and descriptive purposes. They are not intended to be exhaustive and are not intended to limit the scope and spirit of the disclosure. The embodiments were selected and described to best explain the principles of the disclosure and its practical applications. One skilled in the art will recognize that many variations can be made to the disclosure in this specification without departing from the scope and spirit of the disclosure.

The invention claimed is:

1. A peptide comprising the sequence of SEQ ID NO:1.

2. The peptide of claim 1, wherein the peptide exhibits alpha-helical structure.

3. A composition comprising a homopentamer of the peptide of SEQ ID NO:1 in a carrier.

4. The composition of claim 3, further comprising a polynucleotide, wherein the polynucleotide is non-covalently complexed to the homopentamer.

5. The composition of claim 4, further comprising a lipid component, said lipid component comprising a cationic lipid and a neutral lipid.

6. The composition of claim 4, further comprising a cationic polymer.

7. The composition of claim 5, wherein the cationic lipid is selected from 1,2-bis(oleoyloxy)-3-3-(trimethylammonium)propane (DOTAP), 3β-[N-(N'-dimethylaminoethane)-carbamoyl]cholesterol hydrochloride (De-cholesterol), N-[1-(2,3-dioleoyloxy)-propyl]-N,N,N-trimethyl ammonium chloride (DOTMA), 1,2-dioleyloxy-N,N-dimethyl-3-aminopropane (DODMA), 2,3-dioleyloxy-N-[2(sperminecarboxamido)ethyl]-N,N-dimethyl-1-propanaminium trifluoro-acetate (DOSPA), dimethyl dioctadecyl ammonium bromide (DDAB), 1,3-dioleoyloxy-2-(6 carboxy spermyl)-propylamide (DOSPER), and combinations thereof.

8. The composition of claim 5, wherein the neutral lipid is selected from 1,2-dioleoyl-sn-glycero-3phosphoethanolamine (DOPE), dimyristoylphosphatidylcholine (DOPC), distearoylphosphatidylcholine (DSPC), dipalmitoylphosphatidylcholine (DPPC), dimyristoylphosphatidylcholine (DMPC), and combinations thereof.

9. The composition of claim 5, wherein the lipid component is present as liposomal structures and the homopentamer-polynucleotide complexes are encapsulated in the liposomal structures.

10. The composition of claim 9, wherein the size of the liposomal structures is from 100 nm to 500 nm.

11. The composition of claim 9, wherein the polynucleotide is selected from plasmid DNA, siRNA, and mRNA.

12. The composition of claim 9, further comprising a small molecule, wherein the small molecule is non-covalently incorporated in the liposomal membrane, is present in the liposomal aqueous compartment, or is non-covalently associated with the homopentamer.

13. The composition of claim 12, wherein the small molecule is a hydrophobic molecule or a hydrophilic molecule.

14. The composition of claim 12, wherein the composition is suitable for topical administration.

15. A method for introducing a polynucleotide into a cell comprising:
 a) providing a composition of claim 9;
 b) contacting the composition of claim 9 with a cell such that the lipid component is introduced into the cell thereby delivering the polynucleotide to the cell.

16. A kit for introducing molecules into cells comprising:
 a) a composition of claim 3;
 b) a lipid component comprising a cationic lipid and a neutral lipid or a cationic polymer; and
 c) instructions for use of a) and b).

17. The kit of claim 16, further comprising a polynucleotide and/or a small molecule for delivery to cells, and optionally instructions for use of the polynucleotide and/or small molecule.

* * * * *